(12) United States Patent
Stanley et al.

(10) Patent No.: US 10,736,295 B1
(45) Date of Patent: Aug. 11, 2020

(54) HEMP PLANT NAMED 'CW1AS1'

(71) Applicant: Charlotte's Web, Inc., Boulder, CO (US)

(72) Inventors: Joel Stanley, Larkspur, CO (US); Keri Reel, Lafayette, CO (US)

(73) Assignee: Charlotte's Web, Inc., Boulder, CO (US)

( * ) Notice: Subject to any disclaimer, the term of this patent is extended or adjusted under 35 U.S.C. 154(b) by 0 days.

(21) Appl. No.: 16/872,897

(22) Filed: May 12, 2020

Related U.S. Application Data

(63) Continuation of application No. 16/683,429, filed on Nov. 14, 2019, now Pat. No. 10,653,085.

(60) Provisional application No. 62/783,782, filed on Dec. 21, 2018.

(51) Int. Cl.
*A01H 5/10* (2018.01)
*A01H 6/28* (2018.01)

(52) U.S. Cl.
CPC ............... *A01H 6/28* (2018.05); *A01H 5/10* (2013.01)

(58) Field of Classification Search
CPC ........................................................ A01H 6/28
See application file for complete search history.

(56) References Cited

U.S. PATENT DOCUMENTS

PP30,639 P2 * 7/2019 Stanley ............... A01H 5/00
Plt./258

* cited by examiner

*Primary Examiner* — Russell Kallis
(74) *Attorney, Agent, or Firm* — Cooley LLP

(57) ABSTRACT

The present disclosure provides a new and distinct hemp cultivar designated 'CW1AS1'. The present disclosure relates to seeds of the hemp plant 'CW1AS1,' to plants and parts of the hemp plant 'CW1AS1,' and to methods for producing a hemp plant by crossing the hemp plant 'CW1AS1' with itself or other *cannabis* plants. The disclosure further relates to the morphological and physiological characteristics of the new and distinct hemp cultivar and its uses.

23 Claims, 20 Drawing Sheets

HEMP PLANT NAMED 'CW1AS1'

CROSS-REFERENCE TO RELATED APPLICATIONS

This application is a Continuation of U.S. patent application Ser. No. 16/683,429, filed Nov. 14, 2019, now issued as U.S. Pat. No. 10,653,085, which claims priority to and benefit of U.S. Provisional Application No. 62/783,782 filed on Dec. 21, 2018, the entire contents of which are incorporated herein by reference in their entirety for all purposes.

FIELD

The disclosure relates to hemp varieties, hemp extracts, CBD-containing compositions, and methods of producing and using the same.

BACKGROUND OF THE INVENTION

*Cannabis* is a genus of flowering plants that includes at least three species, *Cannabis sativa, Cannabis indica,* and *Cannabis ruderalis* as determined by plant phenotypes and secondary metabolite profiles. Hemp, also known as industrial hemp, is a type of *cannabis* plant grown specifically for the industrial uses of its derived products. In the United States, *Cannabis* is classified as hemp if it accumulates no more than three-tenths of one percent (i.e., 0.3%) concentration of tetrahydrocannabinol (THC) at harvest maturity. Hemp plants can also accumulate high levels of cannabidiol (CBD), which is used in a variety of consumer goods, including food, drinks, dietary supplements and cosmetics.

Hemp production however, remains challenging for farmers. The presence of a single male flower in a hemp field can ruin an entire crop by fertilizing the valuable female flowers. Large scale hemp grows also requires hemp varieties with uniform grows to avoid early or late maturation of a significant portion of the crop. Feminized seeds for high CBD producing lines with resistance to common pests are highly desirable, but not yet widely available.

There remains a need for new hemp varieties to meet the growing demand for fiber and CBD-based products.

BRIEF SUMMARY OF THE INVENTION

This disclosure relates to a new and distinctive hemp cultivar designated as 'CW1AS1'. In some embodiments, the 'CW1AS1' is a *Cannabis sativa* L. plant.

The inventors reproduced the 'CW1AS1' cultivar by utilizing strategic self-fertilizations of the female flowers with pollen derived from the induced male flowers within the proprietary female parent '1AC' cultivar. The 'CW1AS1' plant has been produced by a self-fertilization process that allows for development of 'CW1AS1' seeds at the inventors' grow facilities. The 'CW1AS1' cultivar has also been asexually reproduced via vegetative stem cuttings at the inventors' greenhouses in Wray, Colo. on August 2016.

The present disclosure provides a new and distinctive hemp variety designated as 'CW1AS1'. The present disclosure relates to the seeds of hemp variety 'CW1AS1', to the plants or parts of hemp variety 'CW1AS1', to the plant cells of hemp variety 'CW1AS1', to the plants or plant parts or plant cells having all of the physiological and morphological characteristics of hemp variety 'CW1AS1' and to plants or plant parts or plant cells having all of the physiological and morphological characteristics of plant cells listed in Tables 1-5, including, but not limited to, as determined at the 5% significance level when grown in the same environmental conditions, including when grown side-by-side with a comparison or check *cannabis* and/or hemp plant.

The present disclosure relates to methods for producing a hemp plant and/or seed, by crossing the hemp variety 'CW1AS1' with itself or another *cannabis* and/or hemp plant. A further aspect relates to hybrid hemp plants, and hemp seeds produced by crossing the hemp variety 'CW1AS1' with a *cannabis* and/or hemp plant.

Another aspect of the present disclosure is also directed to a method of producing a cannabinoid extract comprising contacting plants of the hemp variety 'CW1AS1' with a solvent or heat, and producing the cannabinoid extract.

In some embodiments, the present disclosure teaches a seed, plant, plant part, or plant cell of hemp plant variety designated 'CW1AS1', wherein representative seed of the variety has been deposited under NCIMB No. 43291. In some embodiments, the present disclosure teaches that the plant part is a flower.

In some embodiments, the present disclosure teaches a hemp plant or a plant part or a plant cell thereof, having all of the characteristics of the hemp plant variety designated 'CW1AS1' listed in Tables 1-5. In some embodiments, the present disclosure teaches a hemp plant, or a plant part or a plant cell thereof, having all of the physiological and morphological characteristics of the hemp plant of the present disclosure.

In some embodiments, the present disclosure teaches a hemp plant, or a plant part or a plant cell thereof, having all of the physiological and morphological characteristics of the hemp plant variety designated 'CW1AS1', wherein a representative sample of seed of said variety was deposited under NCIMB No. 43291.

In some embodiments, the present disclosure teaches a tissue culture of regenerable cells produced from the plant, plant part or plant cell of the present disclosure, wherein a new plant regenerated from the tissue culture has all of the characteristics of the hemp plant variety designated 'CW1AS1' listed in Tables 1-5 when grown under the same environmental conditions. In some embodiments, the present disclosure teaches a hemp plant regenerated from the tissue culture of the present disclosure, said plant having all the morphological and physiological characteristics of the hemp of the present disclosure. In some embodiments, the present disclosure teaches a hemp plant regenerated from the tissue culture, wherein the regenerated plant has all of the characteristics of the hemp plant variety designated 'CW1AS1', wherein a representative sample of seed of said variety was deposited under NCIMB No. 43291.

In some embodiments, the present disclosure teaches a method for producing a hemp seed, comprising a) selfing the hemp plant of the present disclosure, and b) harvesting the resultant hemp seed. In some embodiments, the present disclosure teaches a hemp seed produced by the method of the present disclosure.

In some embodiments, the present disclosure teaches a method for producing a hemp seed comprising crossing the hemp plant of the present disclosure with a second, distinct plant. In some embodiments, the present disclosure teaches an F1 hemp seed produced by the method of the present disclosure. In some embodiments, the present disclosure teaches an F1 hemp plant, or a part or a plant cell thereof, produced by growing the seed of the present disclosure.

In some embodiments, the present disclosure teaches a method of producing a hemp plant derived from the variety 'CW1AS1,' comprising: a) crossing the plant of the present disclosure, with itself or a second 'CW1AS1' plant to produce progeny seed; b) growing the progeny seed to produce a progeny plant and crossing the progeny plant with itself or a second 'CW1AS1' plant to produce further progeny seed; and c) repeating steps (a) and (b) with sufficient inbreeding until a seed of a hemp plant derived from the variety 'CW1AS1' is produced.

In some embodiments, the present disclosure teaches a method of producing a hemp plant derived from the variety 'CW1AS1', further comprising crossing the hemp plant derived from the variety 'CW1AS1,' with a plant of a different genotype to produce seed of a hybrid plant derived from the hemp variety 'CW1AS1.'

In some embodiments, the present disclosure teaches a method for producing nucleic acids, comprising isolating nucleic acids from the seed, plant, plant part, or plant cell of the present disclosure.

In some embodiments, the present disclosure teaches a hemp plant of the present disclosure, comprising a single locus conversion and otherwise essentially all the morphological and physiological characteristics of the hemp plant of the present disclosure when grown in the same environmental conditions. In some embodiments, the present disclosure teaches that the single locus conversion confers said plant with herbicide resistance. In some embodiments, the present disclosure teaches that the single locus conversion is an artificially mutated gene or nucleotide sequence. In some embodiments, the present disclosure teaches that the single locus conversion is a gene that has been modified through the use of breeding techniques taught in the present disclosure.

In some embodiments, the present disclosure teaches a cultivar of hemp designated 'CW1AS1' as described and detailed in the present disclosure.

In some embodiments, the present disclosure teaches a method of producing a cannabinoid extract, said method comprising the steps a) contacting the plant of the present disclosure with a solvent or heat, thereby producing a cannabinoid extract.

In some embodiments, the present disclosure teaches a dry, non-viable plant part, wherein representative seed of hemp plants producing said dry plant parts has been deposited under NCIMB No. 43291.

In some embodiments, the present disclosure teaches an assemblage of dry, non-viable female inflorescences from a hemp plant variety designated 'CW1AS1' wherein representative seed the variety has been deposited under NCIMB No. 43291. In some embodiments, the present disclosure teaches that a dry, non-viable plant part is an inflorescence.

In some embodiments, the present disclosure teaches a hemp plant of the present disclosure is asexually reproduced. In some embodiments, the present disclosure teaches a hemp plant of the present disclosure is capable of producing an asexual clone of said hemp plant. In some embodiments, the present disclosure teaches that the asexual clone is capable of producing said hemp plant taught in the present disclosure.

DESCRIPTION OF THE DRAWINGS

The accompanying photographs depict characteristics of the new 'CW1AS1' plants as nearly true as possible reproductions. The overall appearance of the 'CW1AS1' plants in the photographs may differ slightly from the color values described in the detailed botanical description of Tables 1-5.

DETAILED DESCRIPTION OF THE INVENTION

Figure 1A:
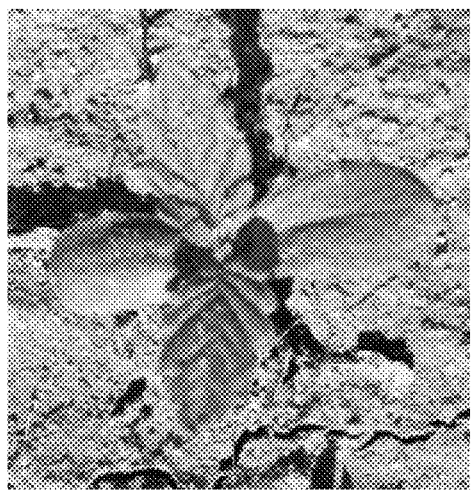
FIG. 1A-1B shows an overall view of the 'CW1AS1' plant at the seedling stage at week 1 (FIG. 1A) and at week 2 (FIG. 1B) as shown from above.
Figure 1B:
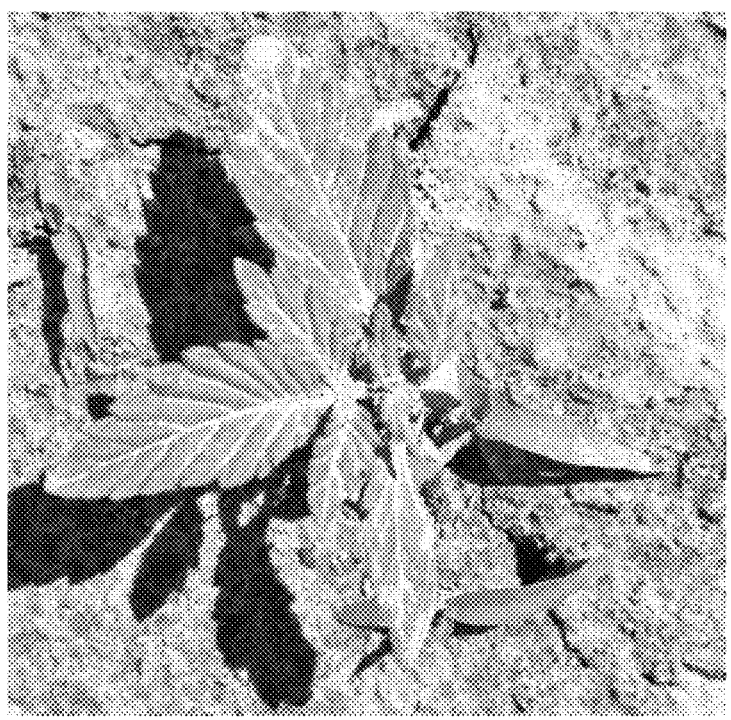
Figure 2:
FIG. 2 shows an overall view of the 'CW1AS1' plant at the early vegetative growth stage at weeks 2-3 with lateral branches and further intermodal growth as shown from above.
Figure 3:
FIG. 3 shows an overall view of the 'CW1AS1' plant during the mid-vegetative growth stage at weeks 5-6 as shown from above.
Figure 4:
FIG. 4 shows an overall view of the 'CW1AS1' plants during the late vegetative growth stage at weeks 8-9 as shown from above.
Figure 5:
FIG. 5 shows an overall view of stem nodes of the 'CW1AS1' plant at the late vegetative growth stage at weeks 8-9 as shown from the side.
Figure 6:
FIG. 6 shows an overall view of the 'CW1AS1' plants close to the vegetative maturity at weeks 12-13 as shown from above.
Figure 7:
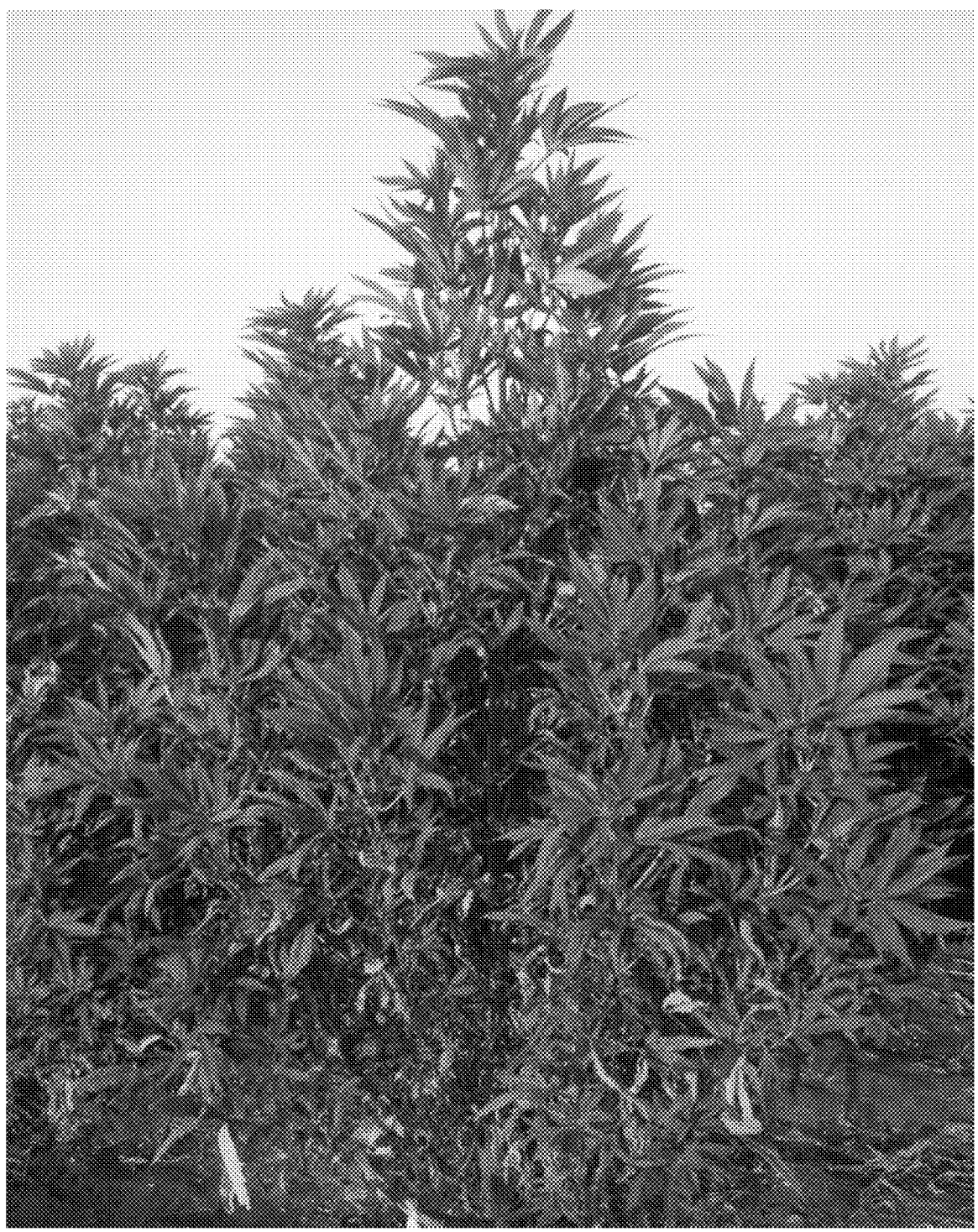
FIG. 7 shows an overall view of the 'CW1AS1' plants close to the vegetative maturity at weeks 12-13 as shown from the side.
Figure 8:
FIG. 8 shows an overall view of upper part (including flowers) of the 'CW1AS1' plants at the early flowering stage at weeks 16-17 as shown from above.
Figure 9:
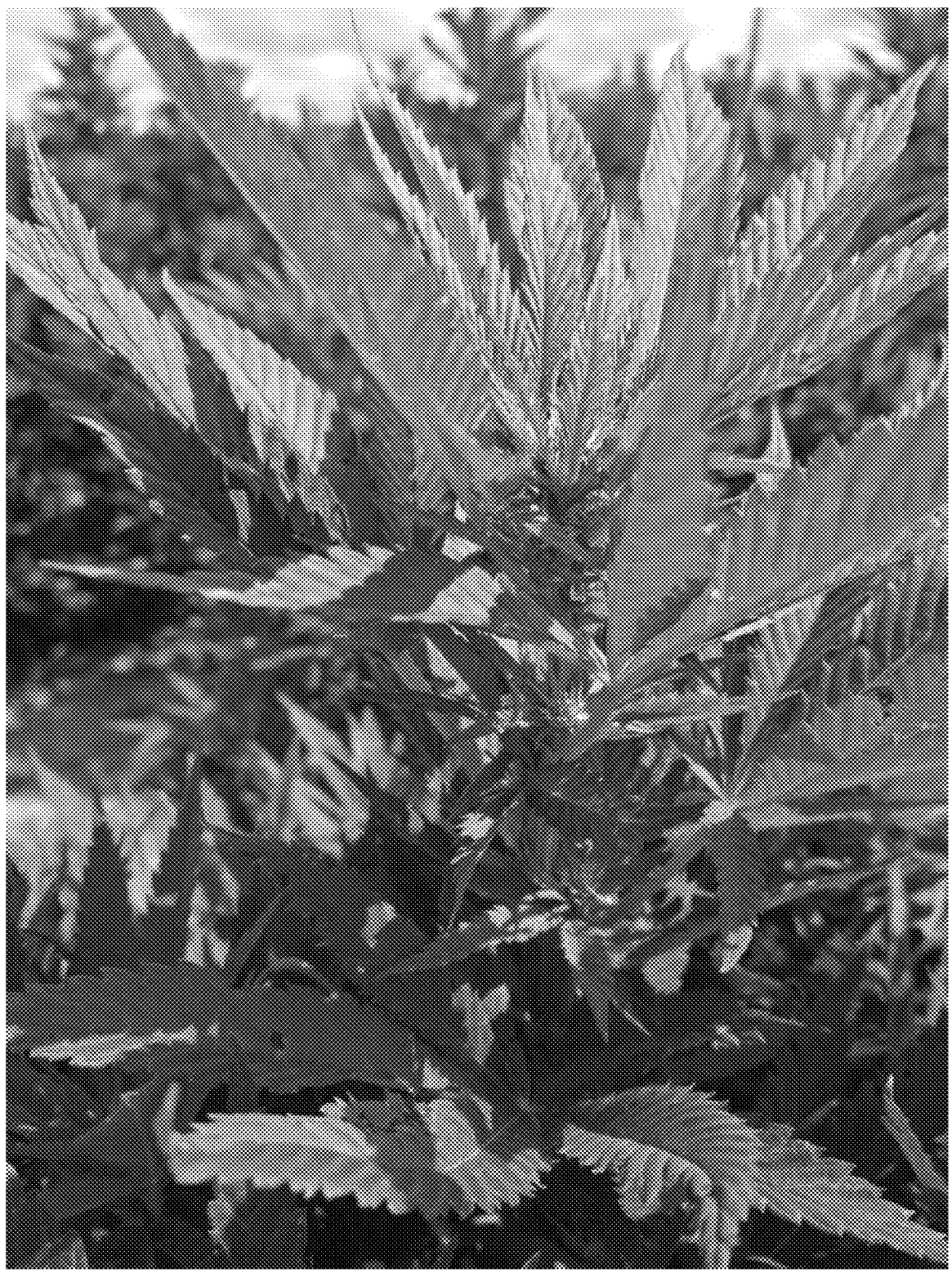
FIG. 9 shows an overall view of upper part (including flowers) of the 'CW1AS1' plants at the early flowering stage as at weeks 16-17 shown from the side.
Figure 10:
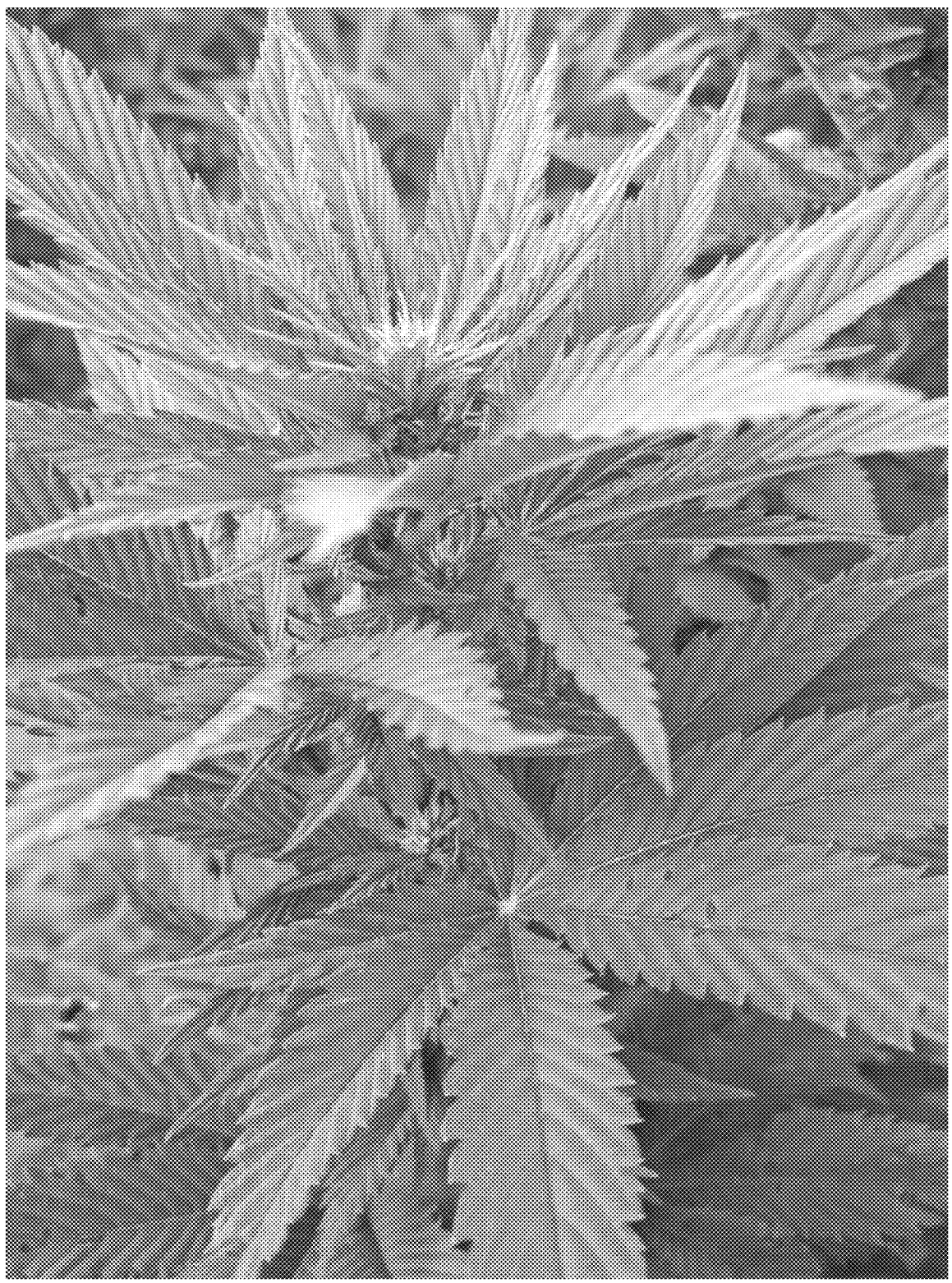
FIG. 10 shows another overall view of upper part (including flowers) of the 'CW1AS1' plants at the early flowering stage as at weeks 16-17 shown from the side.
Figure 11:
FIG. 11 shows an overall view of upper part (including flowers) of the 'CW1AS1' plant with multiple lateral axes dominance (otherwise known as lacking main axis dominance) close to floral maturity at weeks 20-21 as shown from above.
Figure 12:
FIG. 12 shows an overall view of upper part (including flowers) of the 'CW1AS1' plant with main axis dominance close to floral maturity at weeks 20-21 as shown from the side.
Figure 13:
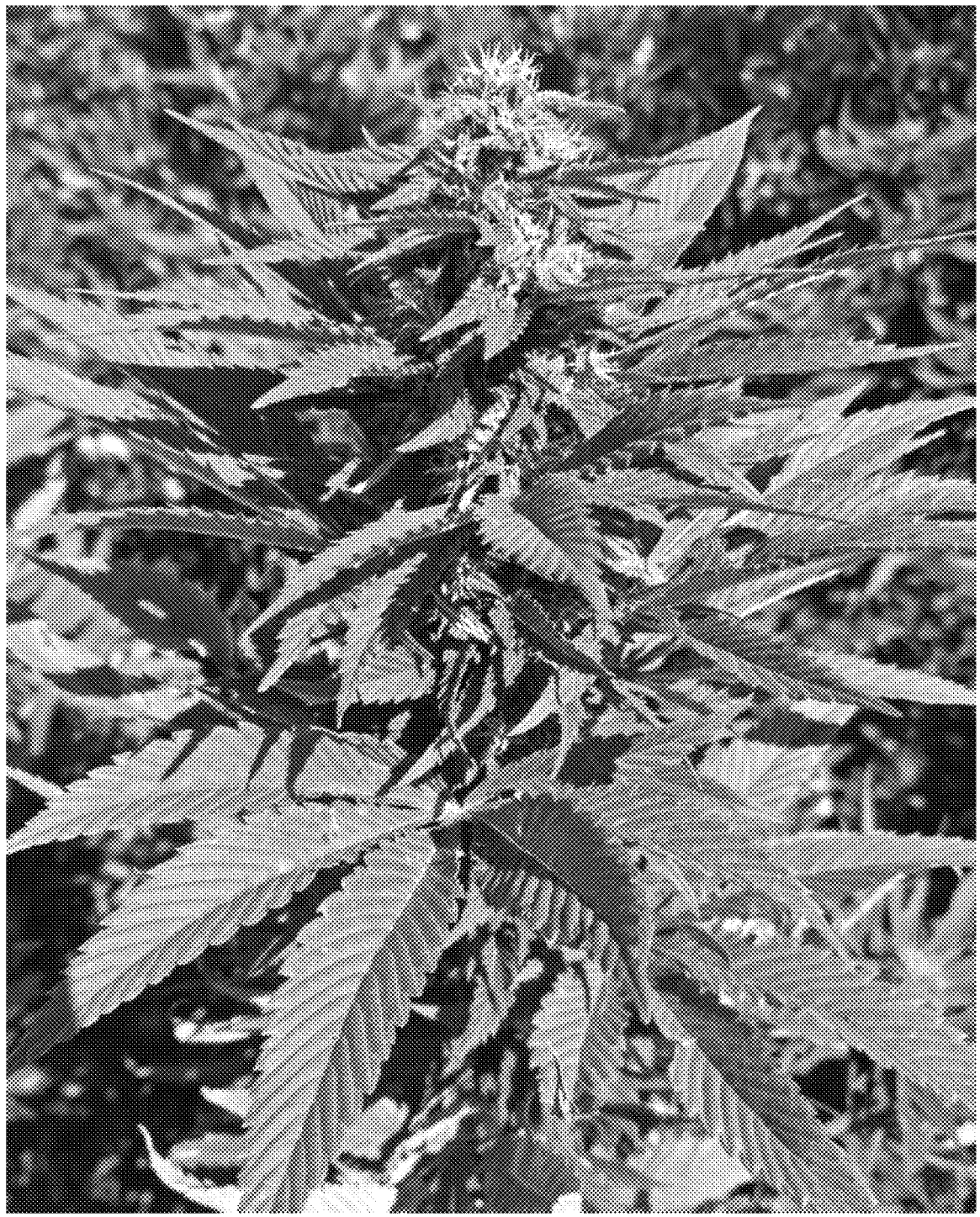
FIG. 13 shows another overall view of upper part (including flowers) of the 'CW1AS1' plant with main axis dominance close to floral maturity at weeks 20-21 as shown from the side.
Figure 14:
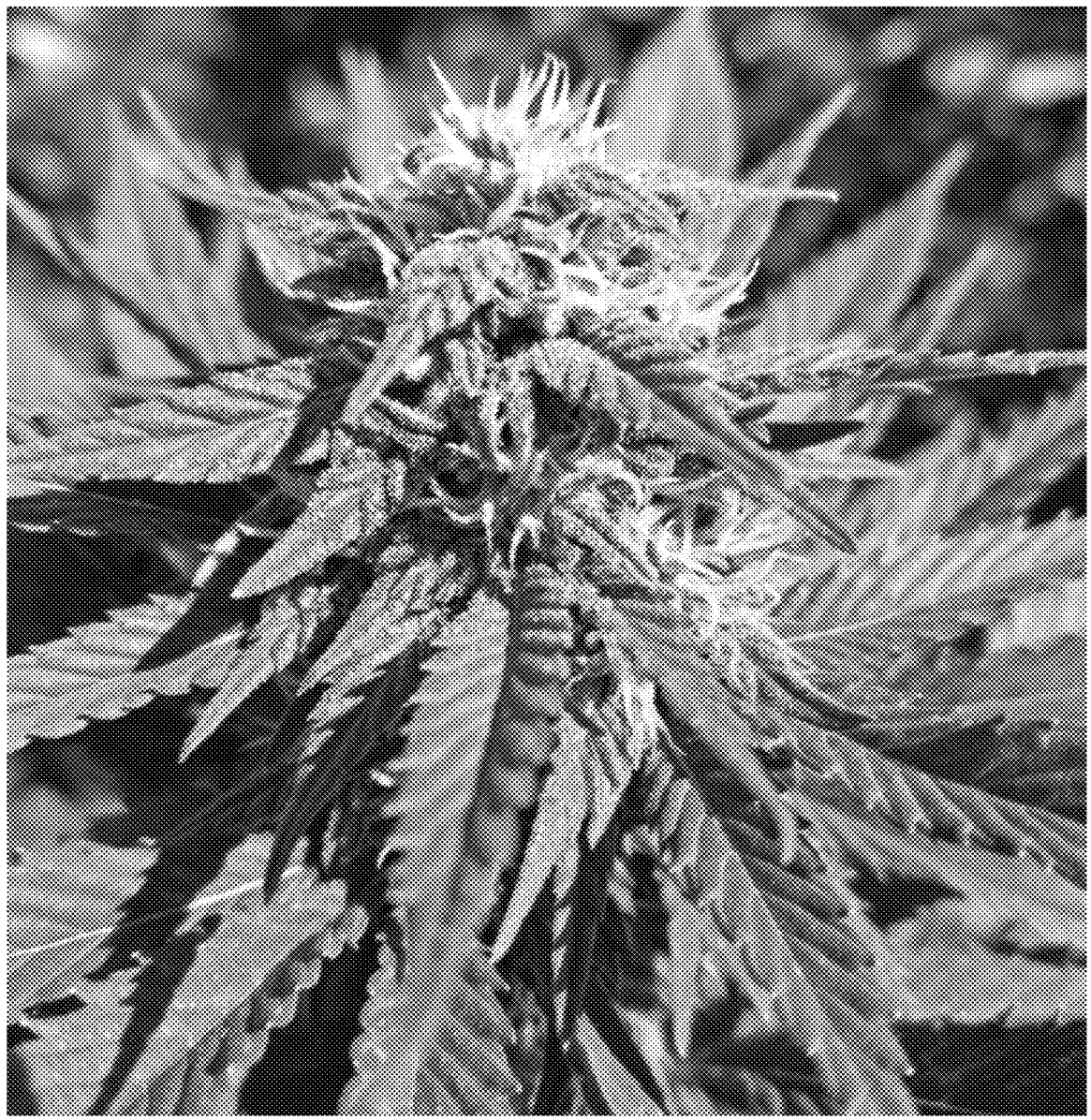
FIG. 14 shows a close view of flowers of the 'CW1AS1' plant close to floral maturity at weeks 20-21 as shown from the side.
Figure 15:
FIG. 15 shows another close view of flowers of the 'CW1AS1' plant with purple coloration in leaves emerging from inflorescences close to floral maturity at weeks 20-21 as shown from above.

All publications, patents and patent applications, including any drawings and appendices, are herein incorporated by reference to the same extent as if each individual publication or patent application was specifically and individually indicated to be incorporated by reference.

The following description includes information that may be useful in understanding the present disclosure. It is not an admission that any of the information provided herein is prior art or relevant to the presently claimed disclosures, or that any publication specifically or implicitly referenced is prior art.

Definitions

As used herein, the verb "comprise" is used in this description and in the claims and its conjugations are used in its non-limiting sense to mean that items following the word are included, but items not specifically mentioned are not excluded.

As used herein, the term "about" refers to plus or minus 10% of the referenced number, unless otherwise stated or otherwise evident by the context (such as when a range would exceed 100% of a possible value or fall below 0% of a possible value). For example, reference to an absolute content of a particular cannabinoid of "about 1%" means that that cannabinoid can be present at any amount ranging from 0.9% to 1.1% content by weight.

The disclosure provides *cannabis* hemp plants. As used herein, the term "plant" refers to plants in the genus of *Cannabis* and plants derived thereof. Such as *cannabis* plants produced via asexual reproduction, tissue culture, and via seed production.

The disclosure provides plant parts. As used herein, the term "plant part" refers to any part of a plant including but not limited to the embryo, shoot, root, stem, seed, stipule, leaf, petal, flower, inflorescence, bud, ovule, bract, trichome, branch, petiole, internode, bark, pubescence, tiller, rhizome, frond, blade, ovule, pollen, stamen, and the like. The two main parts of plants grown in some sort of media, such as soil or vermiculite, are often referred to as the "aboveground" part, also often referred to as the "shoots", and the "below-ground" part, also often referred to as the "roots". Plant parts may also include certain extracts such as kief or hash, which include *cannabis* plant trichomes or glands. In some embodiments, plant part should also be interpreted as referring to individual cells from the plant.

As used herein, the term "plant cell" refers to any totipotent plant cell from a *cannabis* plant. Plant cells of the present disclosure include cells from a *cannabis* plant shoot, root, stem, seed, stipule, leaf, petal, inflorescence, bud, ovule, bract, trichome, petiole, internode. In some embodiments, the disclosed plant cell is from a *cannabis* trichome.

The term "a" or "an" refers to one or more of that entity; for example, "a gene" refers to one or more genes or at least one gene. As such, the terms "a" (or "an"), "one or more" and "at least one" are used interchangeably herein. In addition, reference to "an element" by the indefinite article "a" or "an" does not exclude the possibility that more than one of the elements is present, unless the context clearly requires that there is one and only one of the elements.

The International Code of Zoological Nomenclature defines rank, in the nomenclatural sense, as the level, for nomenclatural purposes, of a taxon in a taxonomic hierarchy (e.g., all families are for nomenclatural purposes at the same rank, which lies between superfamily and subfamily). While somewhat arbitrary, there are seven main ranks defined by the international nomenclature codes: kingdom, phylum/division, class, order, family, genus, and species. Further taxonomic hierarchies used in this disclosure are described below.

The disclosure provides plant cultivars. As used herein, the term "cultivar" means a group of similar plants that by structural features and performance (i.e., morphological and physiological characteristics) can be identified from other varieties within the same species. Furthermore, the term "cultivar" variously refers to a variety, strain or race of plant that has been produced by horticultural or agronomic techniques and is not normally found in wild populations. The terms cultivar, variety, strain and race are often used interchangeably by plant breeders, agronomists and farmers.

The term "variety" as used herein has identical meaning to the corresponding definition in the International Convention for the Protection of New Varieties of Plants (UPOV treaty), of Dec. 2, 1961, as Revised at Geneva on Nov. 10, 1972, on Oct. 23, 1978, and on Mar. 19, 1991. Thus, "variety" means a plant grouping within a single botanical taxon of the lowest known rank, which grouping, irrespective of whether the conditions for the grant of a breeder's right are fully met, can be i) defined by the expression of the characteristics resulting from a given genotype or combination of genotypes, ii) distinguished from any other plant grouping by the expression of at least one of the said characteristics and iii) considered as a unit with regard to its suitability for being propagated unchanged.

The disclosure provides methods for obtaining plant lines. As used herein, the term "line" is used broadly to include, but is not limited to, a group of plants vegetatively propagated from a single parent plant, via tissue culture techniques or a group of inbred plants which are genetically very similar due to descent from a common parent(s) (e.g., by selfing of a genetically stable cultivar. A plant is said to "belong" to a particular line if it (a) is a primary transformant (T0) plant regenerated from material of that line; (b) has a pedigree comprised of a T0 plant of that line; or (c) is genetically very similar due to common ancestry (e.g., via inbreeding or selfing). In this context, the term "pedigree" denotes the lineage of a plant, e.g. in terms of the sexual crosses affected such that a gene or a combination of genes, in heterozygous (hemizygous) or homozygous condition, imparts a desired trait to the plant.

As used herein, the term "inbreeding" refers to the production of offspring via the mating between relatives. The plants resulting from the inbreeding process are referred to herein as "inbred plants" or "inbreds."

The term single allele converted plant as used herein refers to those plants that are developed by a plant breeding technique called backcrossing wherein essentially all of the desired morphological and physiological characteristics of an inbred are recovered in addition to the single allele transferred into the inbred via the backcrossing technique.

The disclosure provides samples. As used herein, the term "sample" includes a sample from a plant, a plant part, a plant cell, or from a transmission vector, or a soil, water or air sample.

The disclosure provides offspring. As used herein, the term "offspring" refers to any plant resulting as progeny from a vegetative or sexual reproduction from one or more parent plants or descendants thereof. For instance, an offspring plant may be obtained by cloning or selfing of a parent plant or by crossing two parent plants and include selfings as well as the F1 or F2 or still further generations. An F1 is a first-generation offspring produced from parents at least one of which is used for the first time as donor of a trait, while offspring of second generation (F2) or subsequent generations (F3, F4, etc.) are specimens produced from selfings of F1's, F2's etc. An F1 may thus be (and usually is) a hybrid resulting from a cross between two true breeding parents (true-breeding is homozygous for a trait), while an F2 may be (and usually is) an offspring resulting from self-pollination of said F1 hybrids.

The disclosure provides methods for crossing a first plant with a second plant. As used herein, the term "cross", "crossing", "cross pollination" or "cross-breeding" refer to the process by which the pollen of one flower on one plant is applied (artificially or naturally) to the ovule (stigma) of a flower on another plant. Backcrossing is a process in which a breeder repeatedly crosses hybrid progeny, for example a first generation hybrid (F1), back to one of the parents of the hybrid progeny. Backcrossing can be used to introduce one or more single locus conversions from one genetic background into another.

In some embodiments, the present disclosure provides methods for obtaining plant genotypes. As used herein, the term "genotype" refers to the genetic makeup of an individual cell, cell culture, tissue, organism (e.g., a plant), or group of organisms.

In some embodiments, the present disclosure provides homozygotes. As used herein, the term "homozygote" refers to an individual cell or plant having the same alleles at one or more loci.

In some embodiments, the present disclosure provides homozygous plants. As used herein, the term "homozygous" refers to the presence of identical alleles at one or more loci in homologous chromosomal segments.

In some embodiments, the present disclosure provides hemizygotes. As used herein, the term "hemizygotes" or "hemizygous" refers to a cell, tissue, organism or plant in which a gene is present only once in a genotype, as a gene in a haploid cell or organism, a sex-linked gene in the heterogametic sex, or a gene in a segment of chromosome in a diploid cell or organism where its partner segment has been deleted.

In some embodiments, the present disclosure provides heterozygotes. As used herein, the terms "heterozygote" and "heterozygous" refer to a diploid or polyploid individual cell or plant having different alleles (forms of a given gene) present at least at one locus. In some embodiments, the cell or organism is heterozygous for the gene of interest that is under control of the synthetic regulatory element.

The disclosure provides self-pollination populations. As used herein, the term "self-crossing", "self-pollinated" or "self-pollination", "self-fertilized" or "self-fertilization" means the pollen of one flower on one plant is applied (artificially or naturally) to the ovule (stigma) of the same or a different flower on the same plant. In some embodiments, plants of the present disclosure are genetically stable, such that pollination between plants of the same cultivar produces offspring are still considered part of the same cultivar. Thus, in some embodiments, 'CW1AS1' is propagated by pollinating several '1AC' female plants with the pollen of one or more '1AC' plants treated to produce a staminate flower. In some embodiments, the present disclosure teaches *cannabis* plants, which are an annual, dioecious, flowering herb. Its leaves are typically palmately compound or digitate, with serrated leaflets. *Cannabis* normally has imperfect flowers, with staminate "male" and pistillate "female" flowers occurring on separate plants. It is not unusual, however, for individual plants of some *cannabis* varieties to separately bear both male and female flowers (i.e., have monoecious plants). Although monoecious plants are often referred to as "hermaphrodites," true hermaphrodites (which are less common in *cannabis*) bear staminate and pistillate structures on individual flowers, whereas monoecious plants bear male and female flowers at different locations on the same plant. In some embodiments, plants of the 'CW1AS1' variety have been feminized, and only produce female inflorescences. In some embodiments, seeds of the 'CW1AS1' variety produce plants that are greater than 99%, 98%, 97%, 96%, 95%, 94%, 93%, 92%, 91%, or 90% female.

As used herein, a "dioecious" plant refers to a plant having either only male flowers (androecious) or female flowers (gynoecious).

As used herein, a "monoecious" plant is a plant having both male and female or bisexual flowers, or both female and male or bisexual flowers. Plants bearing separate flowers of both sexes at the same time are called simultaneously or synchronously monoecious. Plants bearing flowers of one sex at one time are called consecutively monoecious.

The disclosure provides ovules and pollens of plants. As used herein when discussing plants, the term "ovule" refers to the female gametophyte, whereas the term "pollen" means the male gametophyte.

The disclosure provides methods for obtaining plants comprising recombinant genes through transformation. As used herein, the term "transformation" refers to the transfer of nucleic acid (i.e., a nucleotide polymer) into a cell. As used herein, the term "genetic transformation" refers to the transfer and incorporation of DNA, especially recombinant DNA, into a cell.

The disclosure provides transformants comprising recombinant genes. As used herein, the term "transformant" refers to a cell, tissue or organism that has undergone transformation. The original transformant is designated as "T0." Selfing the T0 produces a first transformed generation designated as "F1" or "T1."

In some embodiments, the present disclosure refers to inflorescences from a *cannabis* plant comprising particular cannabinoid and terpene contents (i.e., inflorescences comprising no more than 0.3% THC). In some embodiments, inflorescences, such as dried inflorescences, described as having cannabinoid content are female inflorescences. In some embodiments, the inflorescences are grown "sinsemilla," in the absence of male plants to avoid pollination. Thus in some embodiments, the female inflorescences of the present disclosure are seedless, and in many cases, unpollinated. The term "inflorescence" and "flower" are used interchangeably throughout this document.

Unless otherwise noted, references to cannabinoids in a plant, plant part, extract, or composition of the present disclosure should be understood as references to both the acidic and decarboxylated versions of the compound (e.g., potential THC as determined by the conversion guidelines described in this document, and understood by those skilled in the art). For example, references to high THC contents of a *cannabis* plant in this disclosure should be understood as references to the combined THC and THCA content (accounting for weight loss during decarboxylation).

Detailed Botanical Description

The present disclosure relates to a new and distinct hemp (*Cannabis sativa* L.) cultivar designated as 'CW1AS1'. Whole-plant hemp extracts from 'CW1AS1' contain an assortment of phytocannabinoids (e.g., CBD), terpenes, flavonoids and other minor but valuable hemp compounds that work synergistically to heighten effects of products produced from 'CW1AS1'. This synergistic effect is sometimes referred to as the "entourage effect." 'CW1AS1' extracts can be used to produce a variety of products, including liquid and capsule forms for oral administration, topical products, cosmetic products, infused beverages, sport products and hemp-infused pet treats.

Despite *cannabis* being consumed since at least the third millennium BC, complete scientific corroboration for uses of CBD are still in their infancy. Industry reports suggest CBD is used for a variety of health and wellness purposes, including as a sleep aid, coping with daily stress, fighting anxiety, relieving pain, assisting with cognitive function and boosting immune health. Significant research is currently being conducted at a variety of laboratories on the use of CBD as it relates to epilepsy, Post-Traumatic Stress Disorder (PTSD), cancer, autism, neuroprotection, anti-inflammatory effects, anti-tumor effects and anti-psychotic effects.

'CW1AS1' is a selection resulting from self-fertilization of a ' 1AC' plant that was produced through a series of controlled-crosses using hemp. The primary goal of the breeding program was to develop a new hemp variety with high cannabidiolic acid (CBDA) concentrations and low tetrahydrocannabinolic acid (THCA) concentrations in its mature female flowers.

The new cultivar of 'CW1AS1' was developed by self-fertilizing proprietary hemp cultivar, '1AC', by the inventors via plant hormone manipulation techniques at the inventors' grow facilities. The '1AC' parent had been maintained via asexual reproduction. The presently disclosed 'CW1AS1' variety, was found to be a uniform first selfed generation. Other differences between the newly disclosed 'CW1AS1' and its '1AC' parental line are discussed below.

'CW1AS1' has not been observed under all possible environmental conditions, and the phenotype may vary significantly with variations in environment. The following observations, measurements, and comparisons describe this plant as grown at Wray, Colo. and Broomfield, Colo., when grown in the greenhouse, nursery or field, unless otherwise noted.

Plants for the botanical measurements in the present application are annual plants. In the following description, the color determination is in accordance with The Royal Horticultural Society Colour Chart, Sixth Edition (2015), except where general color terms of ordinary dictionary significance are used.

Persons having skill in the art will be familiar with ways of inducing male flowers, including rodelization or colloidal silver treatments. Briefly, rodelization is the process of stressing female plants to induce pollen sac formations. This can be done by allowing unfertilized female flowers to go beyond harvest maturity in flowering conditions, which will trigger the formation of pollen sacs in the plant's last effort to self-fertilize before the end of the life cycle. Another way of triggering the formation pollen in otherwise feminized plants is to spray the feminized plants at the flowering stage with colloidal silver solutions (e.g. >30 ppm). After several sprays, the plants will start forming pollen sacks. Other forms of silver, such as silver nitrate and silver thiosulfate are also effective. Also, hormones such as gibberellins can be used to induce male flowers on female *cannabis* plants. Additional methods of inducing male flowers have been known to one of ordinary skill in the art, e.g., methods discussed in Ram and Sett (Theoretical and Applied Genetics, 1982, 62(4):369-375) and methods discussed in Ram and Jaiswal (Plant, 1972, 105(3):263-266), each of which is incorporated by reference in its entirety for all purposes.

Breeding History of the Female Parent.

The lineage of proprietary female parent '1AC' comprises four generational crossings. The first crossing was made between a parental female from a cutting of *Cannabis sativa* L. originating in Colorado of unknown parentage ("First Parent Female $F_0$") with a parental male plant ("First Parent Male $F_0$") which originated from a feral hemp population in Colorado with an unknown cannabinoid content. Of the resulting progeny, 40 seeds were germinated and developed into 24 female ("$F_1$ Females") and 16 male ("$F_1$ Males") plants.

For the second crossing, an egg donor from a female clone of *Cannabis sativa* L. with unknown genealogy ("Second Parent Female") was crossed to a healthy vigorous $F_1$ Male from the first cross. Of the resulting offspring, twenty seeds were germinated of which 70% were female ("$F_2$ Females") and 30% were male ("$F_2$ Males").

For the third crossing, a single $F_2$ Female was chosen and crossed with a sibling of First Parent Male $F_0$. Of the resulting progeny, fifty seeds were germinated. Twenty-five seedlings were female ("$F_3$ Females") and 25 were male ("$F_3$ Males").

The fourth generation was produced by crossing two $F_3$ Females that displayed the most vigor and health. Both $F_3$ Females chosen for the cross were short and squat in stature, had medium to broad leaf structure with tight internodes of about ½ inch, and displayed a 70-75 day flowering maturity after flowering initiated. The $F_3$ Female was chosen as the egg donor ("$F_3$-e") for the fourth generation. The $F_3$ female was also chosen as the pollen donor ("$F_3$-p") for the fourth generation. The $F_3$-p female was induced to produce male flowers, thus generating pollen, using heat and erratic photoperiod stress techniques. $F_3$-e was pollinated by $F_3$-p and generated progeny ($F_4$) that were all female with slightly different characteristics. All $F_4$ plants exhibited indica-dominant traits such as medium to broad leaf structure, short squat overall growth habit, and tight internodes with full flower maturity taking roughly 65-70 days after flowering initiated. About 90% of all $F_4$ plants exhibited resistance to pests and diseases and showed great health and vigor throughout the entire lifecycle. Few plants displayed white and/or yellow coloration similar to marbling on the leaves. Of these $F_4$ females, the healthiest and most vigorous individual was chosen to be '1AC'.

Self-Crossing of Induced Female Parental Line. The F4 female parent '1AC' was treated to trigger the formation of intersexual and fully altered male flowers on the newly formed primary lateral branches, thus making self-fertilization possible within the '1AC' plants. The induced '1AC' female plants formed the male flowers, and were consequently self-pollinated to develop seeds. The resulting seeds produce a novel plant designated as 'CW1AS1'. All the observed 'CW1AS1' plants grown from the seeds displayed a very upright plant form from main axis dominance.

Tables 1-5, below, provide the morphological and physiological characteristics of the 'CW1AS1' variety. '1AC', also known as 'CW1A', is provided as a check variety. Unless otherwise noted, measurements below were taken from field-grown plants in Colorado.

TABLE 1

General Characteristics

| Characteristics | New Variety ('CW1AS1') | Parental variety ('1AC') |
| --- | --- | --- |
| Plant life forms | An herbaceous plant (herb). | An herbaceous plant (herb) |
| Plant growth habit | A shrub-like annual plant with a very upright habit and extensive lateral branching. Leaflets are quite wide and contribute to the full, shrub-like appearance. Plants are late maturing and photoperiod dependent for initiation of flowering, typically no less than 11 hours of continuous darkness within a 24 hour period. Main and lateral axes become densely clustered with flower once flowering begins. Main axis is very prominent and dominant. Main axis dominance is the primary growth habit (about two thirds of the observed plants). Lower lateral branches also elongate, contributing to classic shrub-like form and habit, thus looking very Christmas tree-like. About one third of the observed plants show that flowering lateral branches exhibit shared dominance with main axis, which leads to a bushy canopy (This feature is mostly due to planting density or apical axis disturbance). | An upright, shrub-like dioecious annual plant with a rigid branching herbaceous stalk, reaching 0.5-3 meters in height and 0.5-3 meters in width in one growing season |
| Plant origin | Feminized and stabilized progeny obtained through self-fertilization of '1AC' Female Parent. | '1AC' Cannabis sativa L. produced from a series of crosses between a first plant of unknown parentage with a parental male plant from a feral hemp population in Colorado. |
| Plant propagation | Sexually propagated by seeds through self-fertilization (Seed propagation). Also, capable of propagation via cutting and cloning such as vegetative stem cuttings as well as stem cuttings from flowering plants (Vegetative propagation). | Asexually propagated by cutting and cloning such as vegetative stem cuttings as well as stem cuttings from flowering plants |
| Propagation ease | Easy. | Easy |
| Propagation condition | Germination rates of seeds are about 75%-90% (depending on seed treatment such as cleaning and removal of immature seeds), although the germination period from direct seed planting varied from 5 to 15 or more days. Germination rates gradually decrease over time of storage. A spread of seedling maturities is up to three weeks apart in development when early in the season, but with these differences becoming harder to spot later in the season. | Adventitious root structures readily form from stem tissue when submerged in rooting media, including soil, rockwool, aeroponics, etc., when adequate amounts of oxygen and moisture are supplied, and ambient temperatures are between 55-75 degrees Fahrenheit with appropriate lighting conditions. |
| Height (Unit: inch) | An average of 1.4 m, observed range was greater with some stunted plants (especially variegated individuals) with plants up to 1.57 m. | 0.5-3 m at maturity Stalky and bushy with round footprint. With adequate spacing, plant height is approximately equal to width. |
| Width (Unit: inch) | An average of 0.89 m with a range of 0.61 m to 1.17 m. Width depends on planting density. | 0.5-3 m |
| Plant vigor | High. The most vigorous growth in late vegetative stage before flowering stage. | High The most vigorous growth in late vegetative stage before flowering stage. |

TABLE 1-continued

| | General Characteristics | |
|---|---|---|
| Characteristics | New Variety ('CW1AS1') | Parental variety ('1AC') |
| Time to Harvest | Typically, 20-23 weeks from planting. Due to environmental factors in 2018, the time to harvest that year was 160-170 days. | 120-140 days |
| Genetically-modified organism | No. | No. |

TABLE 2

| | Leaf/Foliage | |
|---|---|---|
| Characteristics | New Variety ('CW1AS') | Parental variety ('1AC') |
| Leaf arrangement | Opposite as a seedling and during most of vegetative phase of growth. The opposite arrangement stretches a bit with increased vigor of growth. At the beginning of the flowering stage, the strong tendency of opposite arrangement shifts to alternate arrangement toward the ends of the main axis and lateral branches on new growth. This is a slight skewing of the opposite pattern, as stems exhibits a squarish shape with, what would have been, opposite leaf pairs, still closely emergent on the stem, separated by a short internode. | Alternate with short internodes during early vegetative growth stages especially after cloning Sometimes opposite (vegetative stage) and whorled (flowering stage) leaf positioning depending on growth conditions |
| Leaf shape | Palmately compound. | Palmately compound |
| Leaf structure | Serrated, lanceolate, leaflets evenly bisected by the midvein and with widest point halfway between leaflet attachment to petiole and leaflet apex. | Serrated, lanceolate, pinnately veined leaflets with a medium to dark green upper surface and light green to white green lower surface. |
| Leaf margins | Plane with tooth apices angled toward leaflet apex, that is, that the lamina is planar and that the apices of the toothy margin angle toward the leaflet apex. Jaggedly serrated when leaves are immature, developing into not so jaggedly serrated when leaves/leaflets are mature. Both apical and basal side of tooth are convex, generally. | Plane with tooth apices angled toward leaflet apex Jaggedly serrated when leaves are immature, developing into not so jaggedly serrated when leaves/leaflets are mature Both apical and basal side of tooth are generally convex |
| Leaf hairs | Absent with the naked eye, though stems and petioles minutely pubescent. | Absent with the naked eye, though stems and petioles minutely pubescent. |
| Leaf length with petiole at maturity (Unit: cm) | An average of 22.3 cm, with a range of 18.4 cm to 26.1 cm (longest leaf). | Typically 7.6 cm-17.78 cm. Up to 25.4 cm in the field with optimal growing conditions and at peak vegetative growth |
| Petiole length at maturity (Unit: cm) | An average of 8.7 cm, with a range of 6.3 cm to 12.0 cm (longest petiole). | 5.1 cm-10.2 cm depending on leaf type (on axillary branch node vs main axis, subtending inflorescence, immature/mature, etc.) |
| Petiole color (RHS No.) | Between RHS 145A and 145B. | Between RHS145A and 145B |
| Anthocyanin color and intensity in Petioles | Absent through floral maturity in all observed outdoor plants. Petiole coloration can vary due to nutrient inputs and light conditions. Has been observed in indoor greenhouse | N/A environments. |
| Stipule length at maturity (Unit: mm) | An average of 1.2 mm, with a range of 6 mm to 14 mm (longest stipule). | <1 cm |

TABLE 2-continued

| Leaf/Foliage | | |
|---|---|---|
| Characteristics | New Variety ('CW1AS') | Parental variety ('1AC') |
| Stipule color (RHS No.) | Vibrant green center of stipule is RHS 143A, and the papery white edge is similar to NN155B-NN155C. Within inflorescences, vibrant green center of stipule is RHS 143A-143B, and the papery white edge is similar to NN155B-NN155C. | Linear with slight curvaceous growth. |
| Stipule shape | Spinose, wider at base tapering to the apex but sometimes straight with white, feathery edges. Folded shape down the center, as a 'V' or curling from center to nearly form a tube, vibrant green in color overall. Within inflorescences, stipules subtend (and nearly adhere to) the underside of pistillate flowers. These stipules within inflorescences are wider, shorter, and buried within the densely clustered pistillate inflorescences rendering them not immediately observable without dissection. | Spinose, wider at base tapering to the apex but sometimes straight with white, feathery edges. |
| No. of leaflets | 5, 7, or 9 leaflets. 5 when emergent and in young plants, but many with 7. Once vegetative growth reaches its maturity stage, some plants leaves develop having 9 leaflets. At vegetative maturity, leaves feature 5 or 7 leaflets for the most part, occasionally 9. Mostly 5 in newer leaves on new lateral branches, 7 or 9 on newly emergent leaves on main axis and on vigorous well-established branches of some plants. | 3-7 in immature plants, 5-9 at maturity |
| Middle largest (longest) leaflet ength (Unit: cm) | An average of 13.3 cm at maturity, with a range of 11.1 cm to 15.4 cm. | 6-15 cm |
| Middle largest (longest) leaflet width (Unit: cm) | An average of 3.3 cm at maturity, with a range of 2.5 cm to 4.0 cm. | 2.5-4.0 cm |
| Middle largest (longest) leaflet length/width ratio | An average of about 4:1 at maturity. | About 4:1 |
| No. teeth of middle leaflet | An average of 37 at maturity, with a range of 32 to 42. | 26-37 |
| Leaf (upper side - adaxial) color (RHS No.) | One of the most visually distinct and characteristic attributes of this variety is a colored marbling of the leaves, especially present in early to mid-vegetative growth stages, that is seen on most plants to varying degrees. This marbling is typically a greenish white-yellow coloration similar to RHS 144B, 154D and 2D. Average plants will have 85-100% green foliage with some marbling on leaves. The white-yellow coloration is most likely an absence of photosynthetic chloroplasts in the leaf tissue, is genetically inherited, and is not a symptom of an infection nor pathogen. Solid green leaves are most similar to NN137A and NN137B with some mature leaves closer to 147A. | RHS NN137B Leaf marbling during early to mid-vegetative stages. |

TABLE 2-continued

Leaf/Foliage

| Characteristics | New Variety ('CW1AS') | Parental variety ('1AC') |
| --- | --- | --- |
| | Emergent leaves, especially around inflorescences are from RHS 144A to slightly darker (bluer) than 146A. On miniature leaflets that emerge within inflorescences, darker tips are RHS NN137A to a brighter (yellower) green N144C-N144D at the base of leaflets and in the venation. Some plants feature leaves with increasing purplish coloration that is blended with the dark green color for an overall appearance very similar to RHS N92A. | |
| Leaf (lower side - abaxial) color (RHS No.) | RHS 147B. Slightly lighter (greyer) than RHS NN137D. On miniature leaflets that emerge within inflorescences, RHS 147B-147C leaf and 148B-148C venation. | |
| Leaf glossiness | Low. | Slightly glossy, especially at maturity |
| Vein/midrib shape | Primary vein is straight down the middle of each leaflet. Secondary veins are percurrent, branched alternately from midvein, grow to tooth apex with some forming loops to other secondary veins, and more apparent tertiary venation, especially in mature foliage, Very pronounced on abaxial surface of leaflets. Slightly recessed on adaxial surface. Very finely pubescent. | Midvein is straight down the middle of each leaflet. Secondary veins are percurrent, branched alternately from midvein, grow to tooth apex with some forming loops to other secondary veins, and more apparent tertiary venation, especially in mature leaflets |
| Vein/midrib color (RHS No.) | RHS 147B, also between 146D and 145B. | RHS 145C |
| Aroma | A pleasantly earthy aromatic, strong, peculiar smell with a hint of pine scent. Some consider to be reminiscent of cut grass. | A pleasantly earthy aromatic, strong, peculiar smell with a hint of pine scent |

TABLE 3

Stem

| Characteristics | New Variety ('CW1AS1') | Parental variety ('1AC') |
| --- | --- | --- |
| Stem shape | Main axis stem is squared with rounded edges. Pronounced, singular, longitudinal furrows between nodes on the four flattened surfaces of the square-shaped stems. The discontinuation of the furrowing at the nodes gives the nodal points where leaf petioles and lateral branching emerge a bulky and angular character. At vegetative maturity, stem widens at base, especially so at lower nodal points that have shorter internodal points, takes on a generally more rounded character, but remains green for the most part. Secondary growth is emphasized in the lower portions of the stem once primary growth really takes | A smooth or slightly longitudinally furrowed texture that can vary throughout the plant. Rigid, straight or flexuous Canescent, scabrous, or rough textured in late growth stage |

TABLE 3-continued

| | Stem | |
|---|---|---|
| Characteristics | New Variety ('CW1AS1') | Parental variety ('1AC') |
| | off in newer growth during vegetative development. | |
| Stem diameter at base (Unit: cm) | An average of 4.0 cm (width) and 4.5 cm (depth), with a range of 2.0 cm to 5.5 cm. | 3.0-12 cm in outdoor plants |
| Stem color (RHS No.) | RHS 146D for green and immature stems. Furrows, pubescence, and age of growth produce a slight variance in color: also RHS 137B-137C, 138A, and between 141C and 143A. | Immature RHS 146D Mature RHS 143C |
| Stem pith type | This is highly dependent on the age and/or maturity of the stem. Most mature main stem pith is medium to thick. | Moderate to thick |

TABLE 4

| Inflorescence (Female/Pistillate Flowers) | | |
|---|---|---|
| Characteristics | New Variety ('CW1AS1') | Parental variety ('1AC') |
| Flowering (blooming) habit | Pistillate compound cyme inflorescences are congested with leaf-like bracts, leafy and compact, with the largest inflorescences present on dominant apical stems. Female flowers are small but numerous and take on the coloration present in the vegetation of the specimen (typically green); enclosed and surrounded by a perigonal bract, beaked at the tip; unilocular ovary superior, sessile, with two long filiform stigmatic branches which are white upon emergence and later deteriorating to a rusty reddish-brown. Flowers may form on the entire length of the stem at nodal points; however, inflorescences are most conspicuous at the top of the plant at the ends of the main stem and secondary branches. Flowers and inflorescences are covered with glandular trichomes. Beginning the $15^{th}$ week after planting, the main and lateral axes begin to feature distinct pistillate floral clusters at buds and nodes where before only new vegetative growth budded out. Branching increases toward ends of both lateral and main axes with nodes in these now inflorescent regions starting to be densely clustered with pistillate flowers. Leading up to the $15^{th}$ week, a few plants featured single, enlarged pistillate flowers with stigma at nodes along the main axis. Close to floral maturity (about 132 days after planting in field), large inflorescent clusters are developed in all newer regions of growth in the axillary and terminal buds of the main axis and lateral branches. Miniature, trichomated, tips of leaflets emerge from dense floral clusters. Leaflets number 3, 5, or 7 | Early flower primordia appear at the base of petioles, with a pair of white stigmas emerging from each perigonal bract. Pistillate compound inflorescences are congested pseudospikes with leaf-like bracts, leafy and compact, with the largest inflorescences present on dominant apical stems Female flowers are small but numerous and take on the coloration present in the vegetation of the specimen (typically green); enclosed and surrounded by a fused calyx (perigonal bract), entire, beaked at the tip; unilocular ovary superior, sessile, with two long filiform stigmatic branches which are white upon emergence and later deteriorating to reddish-brown Flowers may form on the entire length of the stem; however, inflorescences are most conspicuous at the top of the plant. Flowers and inflorescences are covered with glandular trichomes |

TABLE 4-continued

| Characteristics | New Variety ('CW1AS1') | Parental variety ('1AC') |
|---|---|---|
| | with many leaves having 5 leaflets. | |
| Proportion of female plants | >99%. Less than 1% of the observed plants featuring pure male flowers or monoecious (female/male) tendencies. | 100% |
| Inflorescence position | Above. Apical portions of main and lateral axes. | Above Apical portions of main and lateral axes |
| Flower arrangement | Cymose | Cymose |
| Number of flowers per plant | Hundreds to thousands of flowers per plant. Multitudinous, congested, with high concentrations on bushier wide inflorescences. | Hundreds to thousands flowers per plant Multitudinous, congested, with high concentrations on bushier wide inflorescence |
| Flower shape | Bilateral symmetry with an overall compressed ovaloid appearance. | Bilateral symmetry with an overall compressed ovaloid appearance |
| Flower (individual pistillate) length (Unit: mm) | Mostly 6 mm to 9 mm, with a range of 4 mm to 10 mm. | 8-14 mm |
| Corolla | Absent in observation | No defined corolla Apetalous pistillate flowers |
| Corolla Color (RHS No.) | N/A | N/A |
| Bract shape (general description) | Bract is photosynthetic, heavily trichomated during peak flowering, persistent and adhering to the gynoecium within, ovate and slightly compressed with a beaked tip from which the pistil emerges. Newly emergent bracts on immature or new flowers are quite smaller, lighter in color, and non-trichomated, sometimes subtended by a stipule Bracts that appear at nodal points on the main axis and at the base of inflorescences just before flowering stage begins are larger, elongated and the beaked-shape is more pronounced. | Bract is photosynthetic, heavily trichomated during peak flowering, persistent and adhering to the gynoecium within, ovate and slightly compressed with a beaked tip from which the pistil emerges. |
| Bract color (RHS No.) | A beautiful gradation from dark green through a lighter, yellowish green, to a pale off-white. Some RHS 137A-D, some 141A-141C, to 143C or 144A-144D or 145A, to 150D or 155A-1555B at lighter base. | Some RHS 137A-137D, some 141A-141C, to 143C or 144A-144D or 145A, to 150D or 155A-155B at lighter base. |
| Stigma shape | Sturdy looking at base, slenderly tapering with minute and fine papillae. Thicker and wider in appearance in general than CW2A. Vibrant yellow green, with almost a golden color past maturity. | Short apical style with two long filiform stigmatic branches At flower maturity, the pistils senesce to a reddish-brown |
| Stigma length (Unit: mm) | 3 mm-6 mm with most being 4 mm-5 mm outdoors, longer indoors up to 10 mm or so This can be heavily influenced by environmental conditions. | 6-9 mm Pollination, and environmental factors effect state of stigma |
| Stigma color (RHS No.) | RHS 150A-150C or 151C-150D when freshly emergent to 8B when around maturity or past maturity, to 164A or 166A-166D or 174A-174B or 175D when senescent. | RHS 150A-150C or 151C-151D when freshly emergent to 8B when around maturity or past maturity, to 164A or 166A-166D or 174A-174B or 175D when senescent |
| Trichome shape | Observation is limited to the human eye. Varying sizes of short-stalked and globular-headed glands, wet in appearance when fresh. | Capitate stalked glandular multiseriate/uniseriate trichomes, especially on flowering inflorescences and perigonial bracts |

TABLE 4-continued

Inflorescence (Female/Pistillate Flowers)

| Characteristics | New Variety ('CW1AS1') | Parental variety ('1AC') |
|---|---|---|
| | Opaquer and increasingly amber tinted on mature and late flowers. Especially abundant on miniature leaves within maturing inflorescences, as well as on pistillate floral bracts (perigonia). | Capitate Sessile glandular trichomes on stems, leaves, and bracts Cystolithic non-glandular trichomes on leaves |
| Trichome color (RHS No.) | RHS NN155A-NN155D, white translucent, to white, to creamy white, to nearly golden white. | Variable Clear, white, translucent at first, as it matures, cloudy to amber as phytochemicals enter the trichome glandular head |
| Terminal bud shape | Dense clusters of emergent pistillate flowers with fresh whitish vegetative stigmas. Bracts and miniature leaves covered with trichomes. Miniature leaves emerging from inflorescences are abundant in this variety. | Terminal buds are naked, vegetative, and mixed depending on life stage (vegetative/flowering) |
| Terminal bud color (RHS No.) | A beautiful gradation from dark green through a lighter, yellowish green, to a pale off-white. Some RHS 137A-137D, some 141A-141C, to 143C or 144A-144D or 145A, to 150D or 155A-155B at lighter base. RHS 150A-150C or 151C-151D freshly emergent | Multicolored stigmas. |
| Pedicel | Absent from observation | Absent |
| Staminate shape | None observed. | None observed. |
| Sepal color (RHS No.) | None observed. | None observed. |
| Pollen description | None observed. | None observed. |
| Marbling of seed | Medium. | N/A |
| Petal description | Absent in observation | Apetalous (petals absent in flowers) |

TABLE 5

Other Characteristics

| Characteristics | New Variety ('CW1AS1') | Parental variety ('1AC') |
|---|---|---|
| Time period and condition of flowering/ blooming | Late flowering. CW1AS1 does not show any immature flowering and only begins to flower 105-110 days after planting. CW1AS1 is highly dependent on day/night length to initiate flowering. | Specifically, a photoperiod of no less than 11 hours of continuous darkness within a 24-hour period. |
| Proportion of hermaphrodite plants | None. | None. |
| Hardiness of plant | Resistant to frost and cold in late vegetative growth stages. Cold resistance increases during the late flowering stage. When subjected to cold temperatures (such as less than 45 degrees Fahrenheit) for longer than 6 hours a day, plants show signs of cold shock and growth rates are reduced. Hardy to tolerant of moist and damp conditions without showing signs of stress if adequate drainage allows damp conditions to be a temporary occurrence. More drought tolerant in clay loam and heavier soils, while less drought tolerant in sandy loam and lighter soils. | Resistant to frost (with nightly temperatures as low as 27 degrees Fahrenheit as long as the temperature rises during the day to melt and dry previous frost found on leaves) Resistant to cold in late vegetative growth stages Cold resistance increases during the late flowering stage When subjected to cold temperatures (such as less than 45 degrees Fahrenheit) for longer than 6 hours a day, plants show signs of cold shock and growth rates are reduced Hardy to tolerate of moist and damp conditions without showing signs of stress if |

TABLE 5-continued

Other Characteristics

| Characteristics | New Variety ('CW1AS1') | Parental variety ('1AC') |
|---|---|---|
| | Over watering is noticeable during the early stages of vegetative growth when plant root structures are more sensitive, or if no adequate drainage exists. | adequate drainage allows damp conditions to be a temporary occurrence More drought tolerant in clay loam and heavier soils, while less drought tolerant in sandy loam and lighter soils Over watering is noticeable during the early stages of vegetative growth when plant root structures are more sensitive, or if no adequate drainage exists |
| Breaking action | Very thick and resilient stem. Can withstand high winds and hail damage without breaking. There is not a single broken stem observed in all sections of fields planted with CW1AS1 throughout the entire season (thousands of plants). | Branches are less flexible Typically, plants do not lean and are very sturdy Plants can tolerate high winds easily without lodging Stem branches can break or split in hail storms, however this is rare |
| Rooting rate after cutting/cloning | 90-95% Plants grows from seeds. Germination time varies from about 5 to 15 days. Direct seed plants have a lengthy deep taproot that grows, leading to good vigor and resiliency. | 92-98% Adventitious roots typically form day 10-day 21 Roots fill a two-inch pot completely in Day 28-45 |
| Total THC and CBD content of inflorescence at floral/harvest maturity | Total CBD content: 6.68%-7.32%, if harvested in target maturity window. Total THC content: 0.20%-0.27%, if harvested in target maturity window. Average Total CBD: Total THC (ratio) = 20:1-35:1 | Total CBD content: 5-8% Total THC content: 0.2-0.3% Total CBD: Total THC (ratio) = 26:1 |

Table 6 includes detailed information of the hemp plant named 'CW1AS1' for profiles of total CBD and THC concentrations as tested on three different flower samples. The claimed 'CW1AS1' variety was tested by the third party service provider, Botanacor Services LLC, to determine flower cannabinoid potency according to the service provider's TM01 procedure using High Performance Liquid Chromatography (HPLC).

Figure 16:
FIG. 16 shows an overall view of the 'CW1AS1' plants at harvest maturity at 20-23 weeks as shown from the side.
Figure 17:
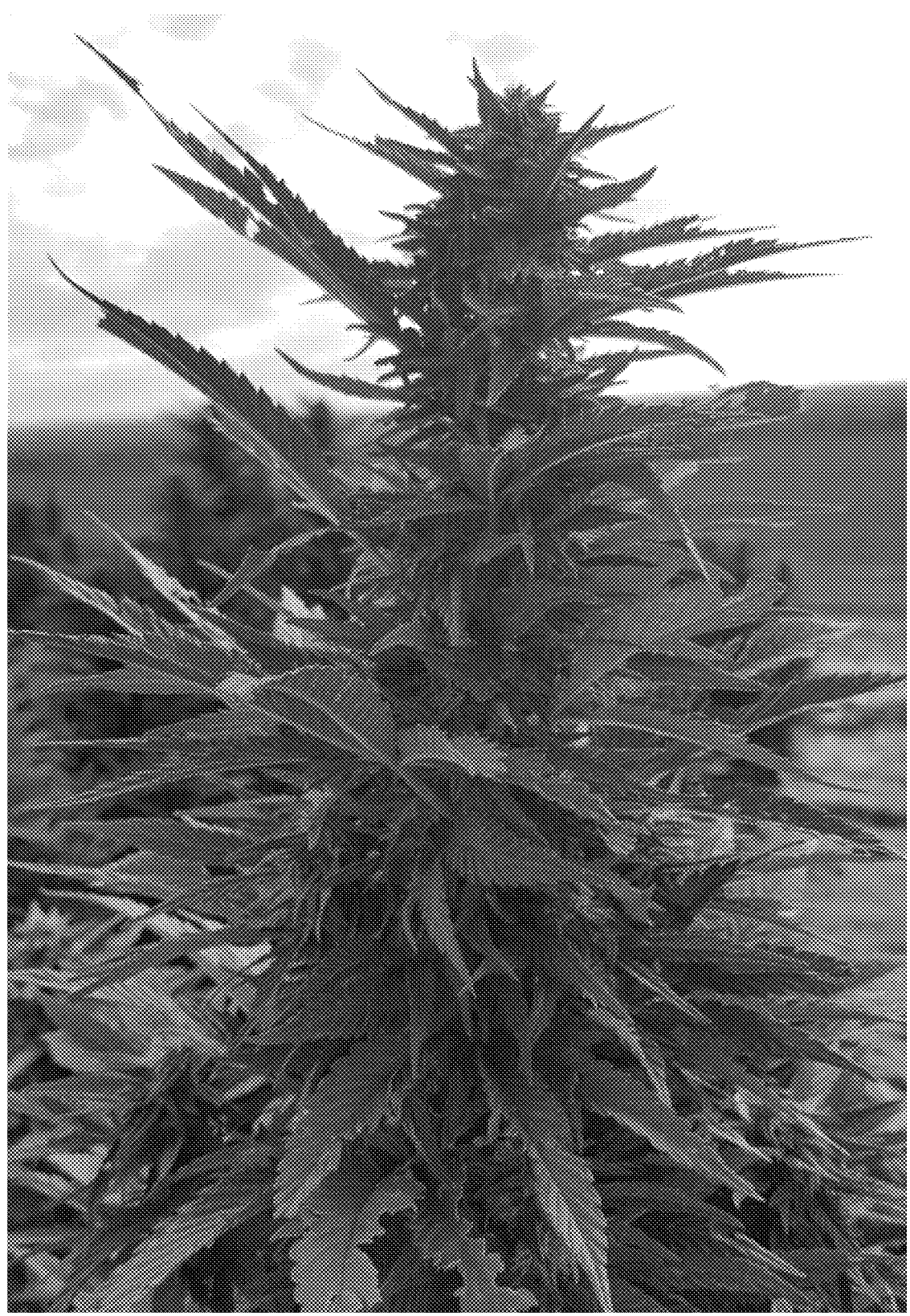
FIG. 17 shows an overall view of upper part (including flowers) of the 'CW1AS1' plant at harvest maturity at 20-23 weeks as shown from the side.
Figure 18:
FIG. 18 shows a close view of flowers of the 'CW1AS1' plant at harvest maturity at 20-23 weeks as shown from the side.
Figure 19:
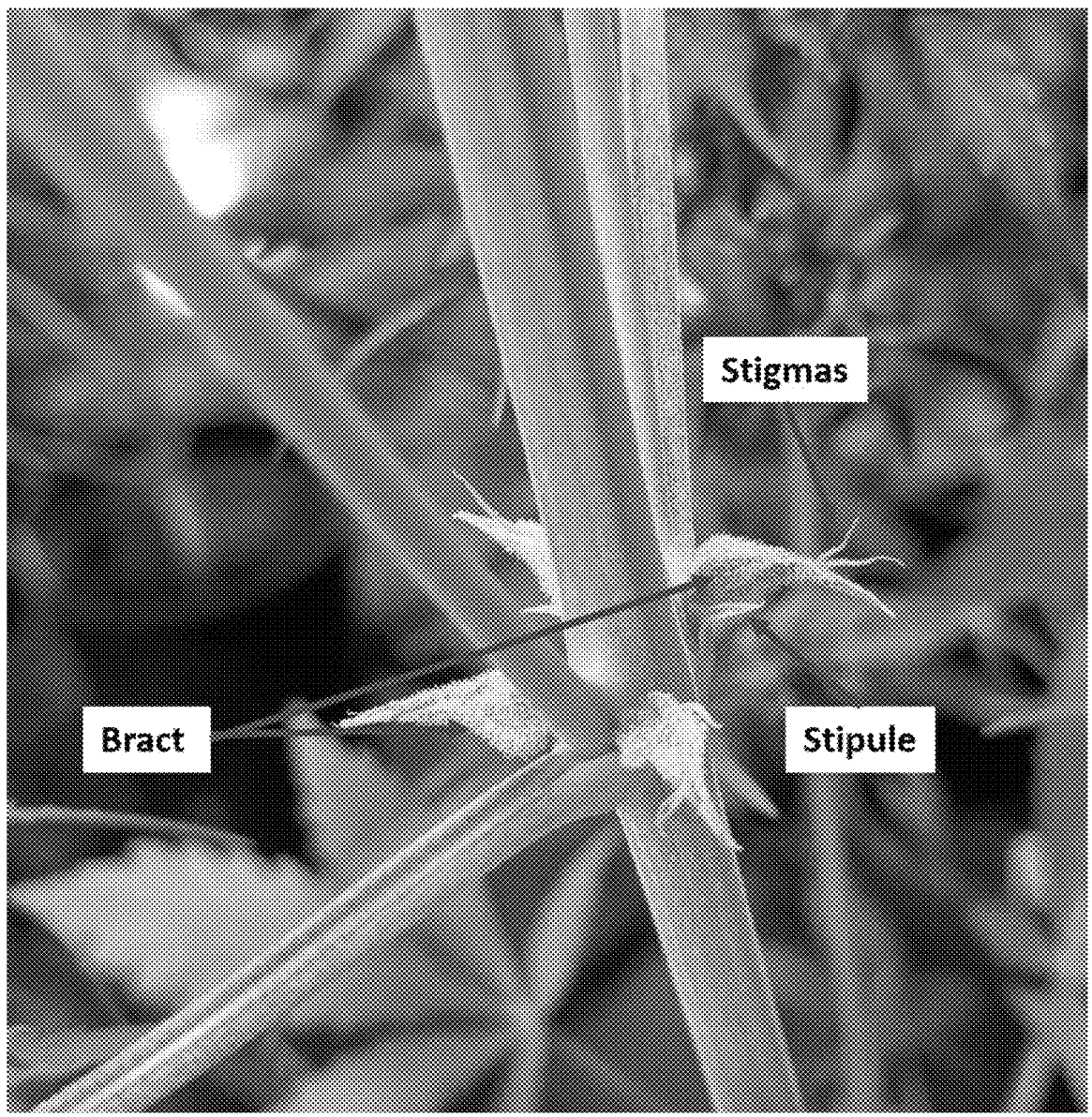
FIG. 19 shows a close view of an industrial hemp internode with emerging female inflorescences. Bract, stipule, and stigmas are labelled. The bract is the trichomated leaf structure enveloping the ovule. The stigma is the sticky antennae-like structure of the female inflorescence for catching pollen, which emerges from the bract opening. The stipule is a small, spike-like leaflet emerging under the bract from the peduncle.
Figure 20:
FIG. 20 shows a top view of the 'CW1AS1' exhibiting leaf marbling phenotype.

As used herein, the term "maturity," "harvest maturity," or "floral maturity" refers to the developmental stage at which the 'CW1AS1' plant is harvested. Persons having skill in the art will recognize maturity based on the plant's morphologies. It is also good practice to conduct periodic cannabinoid content (i.e., potency) tests throughout the development of the plant to ensure that harvest occurs at maturity. The 'CW1AS1' plant is considered to be at harvest maturity when inflorescences begin to take on a 'frosted' appearance, as trichomes develop on bracts, miniature leaves within inflorescences, and lower portions of fan leaves. If the 'frosted' appearance is visible from afar, this could indicate the plant is beyond maturity. The color of trichomes can also be used to determine maturity. Trichomes when first developing on the 'CW1AS1' plant look small and clear, but gradually enlarge, and progressively become 'milkier' and opaque with continued maturation, finally displaying a desiccated appearance and amber color. In the present disclosure, maturity for the 'CW1AS1' plant is defined as the time period between the enlarged clear trichome developmental stage and the opaque/milky trichome developmental stage. Amber trichomes in the 'CW1AS1' plant are an indication of overly mature trichomes. In some embodiments, the ideal time period after planting for floral maturity of the 'CW1AS1' variety is typically around 20-23 weeks after planting seeds in the field, depending on planting date. Strong photoperiod dependent characteristic for initiation of flowering means fixed flowering date in late August in Colorado for the 'CW1AS1' plants. An earlier planting date could extend the time to harvest maturity. Growing conditions throughout the plant's life cycle, nutrient variations, and environmental factors can all influence the amount of time for 'CW1AS1' plants to reach harvest maturity. The present disclosure uses the terms "maturity," "harvest maturity," and "floral maturity" interchangeably. FIGS. 16-18 provide photographs of the 'CW1AS1' plant at harvest maturity. In some embodiments, harvest maturity can encompass any period after the emergence of inflorescences, but before the THC content of any inflorescence surpasses 0.3% THC.

In some instances, the botanical descriptions disclosed herein reflect the range of phenotypical variation observed under indoor and outdoor growth conditions. Total Potential THC/CBD contents presented in this document reflect the total potential (i.e., decarboxylated) THC and CBD content after decarboxylation of the THCA and CBDA contents of the sample. The formula used for this calculation is reproduced below for the Office's convenience. Total THC=THC+(THCA*(0.877)). Total CBD=CBD+(CBDA*(0.877)).

When 'CW1AS1' is compared to the known *cannabis* plant named 'ECUADORIAN *SATIVA*' (U.S. Plant Patent No. 27,475), there are several distinctive characteristics. For example, 'CW1AS1' plant is generally taller than the 'ECUADORIAN SATIVA' plant. While the aroma of 'ECUADORIAN SATIVA' is strongly mephitic with hints of limonene, 'CW1AS1' has a pleasantly earthy aromatic herbal smell with a hint of pine scent. 'CW1AS1' stem diameter at base is bigger than 'ECUADORIAN SATIVA.' However, the flower cyme diameter of 'CW1AS1' is smaller than that of 'ECUADORIAN SATIVA.' Furthermore, there is a significant difference in total THC content between 'CW1AS1' and 'ECUADORIAN SATIVA.' The total THC content of 'CW1AS1' is between 0.26-0.27%, rendering the claimed plant a hemp plant under U.S. law. 'ECUADORIAN SATIVA' on the other hand, accumulates 12.45% total THC, resulting in a different classification of the plant.

When 'CW1AS1' is compared to its parental line '1AC,' there are several distinctive characteristics. For example, 'CW1AS1' has a different leaf arrangement during vegetative stages, longer stipules, and different leaf lengths and vein/midrib colors.

Cannabis Hemp Breeding Methods

In some embodiments, the plants of the present disclosure can be used to produce new plant varieties. In some embodiments, the plants are used to develop new, unique and superior varieties or hybrids with desired phenotypes. As used herein, the term "plant breeding techniques" comprises all of the plant breeding techniques disclosed in this section of the application, and well known to persons having skill in the art. Thus, in some embodiments, plant breeding methods encompass the application of recurrent selection, mass selection, hybridization, open-pollination, backcrossing, pedigree breeding, marker assisted selection breeding, mutation breeding, gene editing, and combinations thereof.

In some embodiments, selection methods, e.g., molecular marker assisted selection, can be combined with breeding methods to accelerate the process. Additional breeding methods have been known to one of ordinary skill in the art, e.g., methods discussed in Chahal and Gosal (Principles and procedures of plant breeding: biotechnological and conventional approaches, CRC Press, 2002, ISBN 084931321X, 9780849313219), Taji et al. (In vitro plant breeding, Routledge, 2002, ISBN 156022908X, 9781560229087), Richards (Plant breeding systems, Taylor & Francis US, 1997, ISBN 0412574500, 9780412574504), Hayes (Methods of Plant Breeding, Publisher: READ BOOKS, 2007, ISBN1406737062, 9781406737066), each of which is incorporated by reference in its entirety for all purposes. The Cannabis genome has been sequenced recently (van Bakel et al., The draft genome and transcriptome of Cannabis sativa, Genome Biology, 12(10):R102, 2011). Molecular markers for cannabis plants are described in Datwyler et al. (Genetic variation in hemp and marijuana (Cannabis sativa L.) according to amplified fragment length polymorphisms, J Forensic Sci. 2006 March; 51(2):371-5.), Pinarkara et al., (RAPD analysis of seized marijuana (Cannabis sativa L.) in Turkey, Electronic Journal of Biotechnology, 12(1), 2009), Hakki et al., (Inter simple sequence repeats separate efficiently hemp from marijuana (Cannabis sativa L.), Electronic Journal of Biotechnology, 10(4), 2007), Datwyler et al., (Genetic Variation in Hemp and Marijuana (Cannabis sativa L.) According to Amplified Fragment Length Polymorphisms, J Forensic Sci, March 2006, 51(2):371-375), Gilmore et al. (Isolation of microsatellite markers in Cannabis sativa L. (marijuana), Molecular Ecology Notes, 3(1): 105-107, March 2003), Pacifico et al., (Genetics and marker-assisted selection of chemotype in Cannabis sativa L.), Molecular Breeding (2006) 17:257-268), and Mendoza et al., (Genetic individualization of Cannabis sativa by a short tandem repeat multiplex system, Anal Bioanal Chem (2009) 393:719-726), each of which is herein incorporated by reference in its entirety for all purposes.

In some embodiments, molecular markers are designed and made, based on the genome of the plants of the present application. In some embodiments, the molecular markers are selected from Isozyme Electrophoresis, Restriction Fragment Length Polymorphisms (RFLPs), Randomly Amplified Polymorphic DNAs (RAPDs), Arbitrarily Primed Polymerase Chain Reaction (AP-PCR), DNA Amplification Fingerprinting (DAF), Sequence Characterized Amplified Regions (SCARs). Amplified Fragment Length Polymorphisms (AFLPs), and Simple Sequence Repeats (SSRs) which are also referred to as Microsatellites, etc. Methods of developing molecular markers and their applications are described by Avise (Molecular markers, natural history, and evolution, Publisher: Sinauer Associates, 2004, ISBN 0878930418, 9780878930418), Srivastava et al. (Plant biotechnology and molecular markers, Publisher: Springer, 2004, ISBN1402019114, 9781402019111), and Vienne (Molecular markers in plant genetics and biotechnology, Publisher: Science Publishers, 2003), each of which is incorporated by reference in its entirety for all purposes.

The molecular markers can be used in molecular marker assisted breeding. For example, the molecular markers can be utilized to monitor the transfer of the genetic material. In some embodiments, the transferred genetic material is a gene of interest, such as genes that contribute to one or more favorable agronomic phenotypes when expressed in a plant cell, a plant part, or a plant.

Details of existing cannabis plants varieties and breeding methods are described in Potter et al. (2011, World Wide Weed: Global Trends in Cannabis Cultivation and Its Control), Holland (2010, The Pot Book: A Complete Guide to Cannabis, Inner Traditions/Bear & Co, ISBN1594778981, 9781594778988), Green I (2009, The Cannabis Grow Bible: The Definitive Guide to Growing Marijuana for Recreational and Medical Use, Green Candy Press, 2009, ISBN 1931160589, 9781931160582), Green II (2005, The Cannabis Breeder's Bible: The Definitive Guide to Marijuana Genetics, Cannabis Botany and Creating Strains for the Seed Market, Green Candy Press, 1931160279, 9781931160278), Starks (1990, Marijuana Chemistry: Genetics, Processing & Potency, ISBN 0914171399, 9780914171393), Clarke (1981, Marijuana Botany, an Advanced Study: The Propagation and Breeding of Distinctive Cannabis, Ronin Publishing, ISBN 091417178X, 9780914171782), Short (2004, Cultivating Exceptional Cannabis: An Expert Breeder Shares His Secrets, ISBN 1936807122, 9781936807123), Cervantes (2004, Marijuana Horticulture: The Indoor/Outdoor Medical Grower's Bible, Van Patten Publishing, ISBN 187882323X, 9781878823236), Franck et al. (1990, Marijuana Grower's Guide, Red Eye Press, ISBN 0929349016, 9780929349015), Grotenhermen and Russo (2002, Cannabis and Cannabinoids: Pharmacology, Toxicology, and Therapeutic Potential, Psychology Press, ISBN 0789015080, 9780789015082), Rosenthal (2007, The Big Book of Buds: More Marijuana Varieties from the World's Great Seed Breeders, ISBN 1936807068, 9781936807062), Clarke, RC (Cannabis: Evolution and Ethnobotany 2013 (In press)), King, J (Cannabible Vols 1-3, 2001-2006), and four volumes of Rosenthal's Big Book of Buds series (2001, 2004, 2007, and 2011), each of which is herein incorporated by reference in its entirety for all purposes.

Classical breeding methods can be included in the present disclosure to introduce one or more recombinant expression cassettes of the present disclosure into other plant varieties, or other close-related species that are compatible to be crossed with the transgenic plant. In some embodiments, the recombinant expression cassette can encode for a desirable phenotype, including herbicide resistance, disease or pest resistance, insect resistance, resistance to antibiotics, or additional traits, as disclosed in this application.

In some embodiments, said method comprises (i) crossing any one of the plants of the present disclosure comprising the expression cassette as a donor to a recipient plant line to create a F1 population; (ii) selecting offspring that have expression cassette. Optionally, the offspring can be further selected by testing the expression of the gene of interest. Thus in some embodiments, the present disclosure teaches crossing a transgenic plant with the presently disclosed 'CW1AS1' plant.

In some embodiments, complete chromosomes of the donor plant are transferred. For example, the transgenic plant with the expression cassette can serve as a male or female parent in a cross pollination to produce offspring plants, wherein by receiving the transgene from the donor plant, the offspring plants have the expression cassette.

In a method for producing plants having the expression cassette, protoplast fusion can also be used for the transfer of the transgene from a donor plant to a recipient plant. Protoplast fusion is an induced or spontaneous union, such as a somatic hybridization, between two or more protoplasts (cells in which the cell walls are removed by enzymatic treatment) to produce a single bi- or multi-nucleate cell. The fused cell that may even be obtained with plant species that cannot be interbred in nature is tissue cultured into a hybrid plant exhibiting the desirable combination of traits. More specifically, a first protoplast can be obtained from a plant having the expression cassette. A second protoplast can be obtained from a second plant line, optionally from another plant species or variety, preferably from the same plant species or variety, that comprises commercially desirable characteristics, such as, but not limited to disease resistance, insect resistance, valuable grain characteristics (e.g., increased seed weight and/or seed size) etc. The protoplasts are then fused using traditional protoplast fusion procedures, which are known in the art to produce the cross.

Alternatively, embryo rescue may be employed in the transfer of the expression cassette from a donor plant to a recipient plant. Embryo rescue can be used as a procedure to isolate embryos from crosses wherein plants fail to produce viable seed. In this process, the fertilized ovary or immature seed of a plant is tissue cultured to create new plants (see Pierik, 1999, In vitro culture of higher plants, Springer, ISBN 079235267x, 9780792352679, which is incorporated herein by reference in its entirety).

In some embodiments, the recipient plant is an elite line having one or more certain desired traits. Examples of desired traits include but are not limited to those that result in increased biomass production, production of specific chemicals, increased seed production, improved plant material quality, increased seed oil content, etc. Additional examples of desired traits include pest resistance, vigor, development time (time to harvest), enhanced nutrient content, novel growth patterns, aromas or colors, salt, heat, drought and cold tolerance, and the like. Desired traits also include selectable marker genes (e.g., genes encoding herbicide or antibiotic resistance used only to facilitate detection or selection of transformed cells), hormone biosynthesis genes leading to the production of a plant hormone (e.g., auxins, gibberellins, cytokinins, abscisic acid and ethylene that are used only for selection), or reporter genes (e.g. luciferase, β-glucuronidase, chloramphenicol acetyl transferase (CAT, etc.). The recipient plant can also be a plant with preferred chemical compositions, e.g., compositions preferred for medical use or industrial applications.

Classical breeding methods can be used to produce new varieties of *cannabis* according to the present disclosure. Newly developed F1 hybrids can be reproduced via asexual reproduction.

Open-Pollinated Populations. The improvement of open-pollinated populations of such crops as rye, many maizes and sugar beets, herbage grasses, legumes such as alfalfa and clover, and tropical tree crops such as cacao, coconuts, oil palm and some rubber, depends essentially upon changing gene-frequencies towards fixation of favorable alleles while maintaining a high (but far from maximal) degree of heterozygosity. Uniformity in such populations is impossible and trueness-to-type in an open-pollinated variety is a statistical feature of the population as a whole, not a characteristic of individual plants. Thus, the heterogeneity of open-pollinated populations contrasts with the homogeneity (or virtually so) of inbred lines, clones and hybrids.

Population improvement methods fall naturally into two groups, those based on purely phenotypic selection, normally called mass selection, and those based on selection with progeny testing. Interpopulation improvement utilizes the concept of open breeding populations; allowing genes to flow from one population to another. Plants in one population (cultivar, strain, ecotype, or any germplasm source) are crossed either naturally (e.g., by wind) or by hand or by bees (commonly *Apis mellifera* L. or *Megachile rotundata* F.) with plants from other populations. Selection is applied to improve one (or sometimes both) population(s) by isolating plants with desirable traits from both sources.

There are basically two primary methods of open-pollinated population improvement. First, there is the situation in which a population is changed en masse by a chosen selection procedure. The outcome is an improved population that is indefinitely propagatable by random-mating within itself in isolation. Second, the synthetic variety attains the same end result as population improvement but is not itself propagatable as such; it has to be reconstructed from parental lines or clones. These plant breeding procedures for improving open-pollinated populations are well known to those skilled in the art and comprehensive reviews of breeding procedures routinely used for improving cross-pollinated plants are provided in numerous texts and articles, including: Allard, *Principles of Plant Breeding*, John Wiley & Sons, Inc. (1960); Simmonds, *Principles of Crop Improvement*, Longman Group Limited (1979); Hallauer and Miranda, *Quantitative Genetics in Maize Breeding*, Iowa State University Press (1981); and, Jensen, *Plant Breeding Methodology*, John Wiley & Sons, Inc. (1988).

Mass Selection. In mass selection, desirable individual plants are chosen, harvested, and the seed composited without progeny testing to produce the following generation. Since selection is based on the maternal parent only, and there is no control over pollination, mass selection amounts to a form of random mating with selection. As stated herein, the purpose of mass selection is to increase the proportion of superior genotypes in the population.

Mutation breeding is another method of introducing new traits into the hemp plants of the present disclosure. Mutations that occur spontaneously or are artificially induced can be useful sources of variability for a plant breeder. The goal of artificial mutagenesis is to increase the rate of mutation for a desired characteristic. Mutation rates can be increased by many different means including temperature, long-term seed storage, tissue culture conditions, radiation; such as X-rays, Gamma rays (e.g., cobalt 60 or cesium 137), neutrons, (product of nuclear fission by uranium 235 in an atomic reactor), Beta radiation (emitted from radioisotopes such as phosphorus 32 or carbon 14), or ultraviolet radiation (preferably from 2500 to 2900 nm), or chemical mutagens (such as base analogues (5-bromo-uracil)), related compounds (8-ethoxy caffeine), antibiotics (streptonigrin), alkylating agents (sulfur mustards, nitrogen mustards, epoxides, ethyleneamines, sulfates, sulfonates, sulfones, lactones), azide, hydroxylamine, nitrous acid, or acridines. Once a desired trait is observed through mutagenesis the trait may then be incorporated into existing germplasm by traditional breeding techniques. Details of mutation breeding can be found in Allard, *Principles of Plant Breeding*, John Wiley & Sons, Inc. (1960). In addition, mutations created in other hemp plants may be used to produce a backcross conversion of hemp plants having all phenotypes of the 'CW1AS1' line while comprising the mutation obtained from the other hemp plants.

Additional methods include, but are not limited to, expression vectors introduced into plant tissues using a direct gene transfer method, such as microprojectile-mediated delivery, DNA injection, electroporation, and the like. More preferably, expression vectors are introduced into plant tissues by using either microprojectile-mediated delivery with a biolistic device or by using *Agrobacterium*-mediated transformation. Transformant plants obtained with the protoplasm of the subject hemp plants are intended to be within the scope of the embodiments of the application.

Synthetics. A synthetic variety is produced by crossing inter se a number of genotypes selected for good combining ability in all possible hybrid combinations, with subsequent maintenance of the variety by open pollination. Whether parents are (more or less inbred) seed-propagated lines, as in some sugar beet and beans (*Vicia*) or clones, as in herbage grasses, clovers and alfalfa, makes no difference in principle. Parents are selected on general combining ability, sometimes by test crosses or toperosses, more generally by polycrosses. Parental seed lines may be deliberately inbred (e.g. by selfing or sib crossing). However, even if the parents are not deliberately inbred, selection within lines during line maintenance will ensure that some inbreeding occurs. Clonal parents will, of course, remain unchanged and highly heterozygous.

Whether a synthetic can go straight from the parental seed production plot to the farmer or must first undergo one or two cycles of multiplication depends on seed production and the scale of demand for seed. In practice, grasses and clovers are generally multiplied once or twice and are thus considerably removed from the original synthetic.

While mass selection is sometimes used, progeny testing is generally preferred for polycrosses, because of their operational simplicity and obvious relevance to the objective, namely exploitation of general combining ability in a synthetic.

The numbers of parental lines or clones that enter a synthetic vary widely. In practice, numbers of parental lines range from 10 to several hundred, with 100-200 being the average. Broad based synthetics formed from 100 or more clones would be expected to be more stable during seed multiplication than narrow based synthetics.

Pedigreed varieties. A pedigreed variety is a superior genotype developed from selection of individual plants out of a segregating population followed by propagation and seed increase of self-pollinated offspring and careful testing of the genotype over several generations. This is an open pollinated method that works well with naturally self-pollinating species. This method can be used in combination with mass selection in variety development. Variations in pedigree and mass selection in combination are the most common methods for generating varieties in self-pollinated crops.

Hybrids. A hybrid is an individual plant resulting from a cross between parents of differing genotypes. Commercial hybrids are now used extensively in many crops, including corn (maize), sorghum, sugar beet, sunflower and broccoli. Hybrids can be formed in a number of different ways, including by crossing two parents directly (single cross hybrids), by crossing a single cross hybrid with another parent (three-way or triple cross hybrids), or by crossing two different hybrids (four-way or double cross hybrids).

Strictly speaking, most individuals in an out breeding (i.e., open-pollinated) population are hybrids, but the term is usually reserved for cases in which the parents are individuals whose genomes are sufficiently distinct for them to be recognized as different species or subspecies. Hybrids may be fertile or sterile depending on qualitative and/or quantitative differences in the genomes of the two parents. Heterosis, or hybrid vigor, is usually associated with increased heterozygosity that results in increased vigor of growth, survival, and fertility of hybrids as compared with the parental lines that were used to form the hybrid. Maximum heterosis is usually achieved by crossing two genetically different, highly inbred lines.

Targeting Induced Local Lesions in Genomes (TILLING). Breeding schemes of the present disclosure can include crosses with TILLING® plant lines. TILLING® is a method in molecular biology that allows directed identification of mutations in a specific gene. TILLING® was introduced in 2000, using the model plant *Arabidopsis thaliana*. TILLING® has since been used as a reverse genetics method in other organisms such as zebrafish, corn, wheat, rice, soybean, tomato and lettuce. The method combines a standard and efficient technique of mutagenesis with a chemical mutagen (e.g., Ethyl methanesulfonate (EMS)) with a sensitive DNA screening-technique that identifies single base mutations (also called point mutations) in a target gene. EcoTILLING is a method that uses TILLING® techniques to look for natural mutations in individuals, usually for population genetics analysis (see Comai, et al., 2003 The Plant Journal 37, 778-786; Gilchrist et al. 2006 Mol. Ecol. 15, 1367-1378; Mejlhede et al. 2006 Plant Breeding 125, 461-467; Nieto et al. 2007 BMC Plant Biology 7, 34-42, each of which is incorporated by reference hereby for all purposes). DEcoTILLING is a modification of TILLING® and EcoTILLING which uses an inexpensive method to identify fragments (Garvin et al., 2007, DEcoTILLING: An inexpensive method for SNP discovery that reduces ascertainment bias. Molecular Ecology Notes 7, 735-746). More detailed description on methods and compositions on TILLING® can be found in U.S. Pat. No. 5,994,075, US 2004/0053236 A1, WO 2005/055704, and WO 2005/048692, each of which is hereby incorporated by reference for all purposes.

In some embodiments, TILLING® can also be utilized for plants of the *cannabis* genus including hemp plants. Thus in some embodiments, the breeding methods of the present disclosure include breeding with one or more TILLING plant lines with one or more identified mutations.

Gene editing technologies. Breeding and selection schemes of the present disclosure can include crosses with plant lines that have undergone genome editing. In some embodiments, the breeding and selection methods of the present disclosure are compatible with plants that have been modified using any gene and/or genome editing tool, including, but not limited to: ZFNs, TALENS, CRISPR, and Mega nuclease technologies. In some embodiments, persons having skill in the art will recognize that the breeding methods of the present disclosure are compatible with many other gene editing technologies. In some embodiments, the present disclosure teaches gene-editing technologies can be applied for a single locus conversion, for example, conferring hemp plant with herbicide resistance. In some embodiments, the present disclosure teaches that the single locus conversion is an artificially mutated gene or nucleotide sequence that has been modified through the use of breeding techniques taught herein.

In some embodiments, the breeding and selection methods of the present disclosure are compatible with plants that have been modified through Zinc Finger Nucleases. Three variants of the ZFN technology are recognized in plant breeding (with applications ranging from producing single mutations or short deletions/insertions in the case of ZFN-1 and -2 techniques up to targeted introduction of new genes in the case of the ZFN-3 technique); 1) ZFN-1: Genes encoding ZFNs are delivered to plant cells without a repair template. The ZFNs bind to the plant DNA and generate site specific double-strand breaks (DSBs). The natural DNA-repair process (which occurs through nonhomologous end-joining, NHEJ) leads to site specific mutations, in one or only a few base pairs, or to short deletions or insertions; 2) ZFN-2: Genes encoding ZFNs are delivered to plant cells along with a repair template homologous to the targeted area, spanning a few kilo base pairs. The ZFNs bind to the plant DNA and generate site-specific DSBs. Natural gene repair mechanisms generate site-specific point mutations e.g. changes to one or a few base pairs through homologous recombination and the copying of the repair template; and 3) ZFN-3: Genes encoding ZFNs are delivered to plant cells along with a stretch of DNA which can be several kilo base pairs long and the ends of which are homologous to the DNA sequences flanking the cleavage site. As a result, the DNA stretch is inserted into the plant genome in a site-specific manner.

In some embodiments, the breeding and selection methods of the present disclosure are compatible with plants that have been modified through Transcription activator-like (TAL) effector nucleases (TALENs). TALENS are polypeptides with repeat polypeptide arms capable of recognizing and binding to specific nucleic acid regions. By engineering the polypeptide arms to recognize selected target sequences, the TAL nucleases can be used to direct double stranded DNA breaks to specific genomic regions. These breaks can then be repaired via recombination to edit, delete, insert, or otherwise modify the DNA of a host organism. In some embodiments, TALENSs are used alone for gene editing (e.g., for the deletion or disruption of a gene). In other embodiments, TALs are used in conjunction with donor sequences and/or other recombination factor proteins that will assist in the Non-homologous end joining (NHEJ) process to replace the targeted DNA region. For more information on the TAL-mediated gene editing compositions and methods of the present disclosure, see U.S. Pat. Nos. 8,440,432; 8,450,471; 8,586,526; 8,586,363; 8,592,645; 8,697,853; 8,704,041; 8,921,112; and 8,912,138, each of which is hereby incorporated in its entirety for all purposes.

In some embodiments, the breeding and selection methods of the present disclosure are compatible with plants that have been modified through Clustered Regularly Interspaced Short Palindromic Repeats (CRISPR) or CRISPR-associated (Cas) gene editing tools. CRISPR proteins were originally discovered as bacterial adaptive immunity systems which protected bacteria against viral and plasmid invasion. There are at least three main CRISPR system types (Type I, II, and III) and at least 10 distinct subtypes (Makarova, K. S., et. al., Nat Rev Microbiol. 2011 May 9; 9(6):467-477). Type I and III systems use Cas protein complexes and short guide polynucleotide sequences to target selected DNA regions. Type II systems rely on a single protein (e.g. Cas9) and the targeting guide polynucleotide, where a portion of the 5' end of a guide sequence is complementary to a target nucleic acid. For more information on the CRISPR gene editing compositions and methods of the present disclosure, see U.S. Pat. Nos. 8,697,359; 8,889,418; 8,771,945; and 8,871,445, each of which is hereby incorporated in its entirety for all purposes.

In some embodiments, the breeding and selection methods of the present disclosure are compatible with plants that have been modified through meganucleases. In some embodiments, meganucleases are engineered endonucleases capable of targeting selected DNA sequences and inducing DNA breaks. In some embodiments, new meganucleases targeting specific regions are developed through recombinant techniques which combine the DNA binding motifs from various other identified nucleases. In other embodiments, new meganucleases are created through semi-rational mutational analysis, which attempts to modify the structure of existing binding domains to obtain specificity for additional sequences. For more information on the use of meganucleases for genome editing, see Silva et al., 2011 Current Gene Therapy 11 pg 11-27; and Stoddard et al., 2014 Mobile DNA 5 pg 7, each of which is hereby incorporated in its entirety for all purposes.

Plant Transformation

Hemp plants of the present disclosure, such as 'CW1AS1' can be further modified by introducing one or more transgenes which when expressed lead to desired phenotypes. The most common method for the introduction of new genetic material into a plant genome involves the use of living cells of the bacterial pathogen *Agrobacterium tumefaciens* to literally inject a piece of DNA, called transfer or T-DNA, into individual plant cells (usually following wounding of the tissue) where it is targeted to the plant nucleus for chromosomal integration. There are numerous patents governing *Agrobacterium* mediated transformation and particular DNA delivery plasmids designed specifically for use with *Agrobacterium*—for example, U.S. Pat. No. 4,536,475, EP0265556, EP0270822, WO8504899, WO8603516, U.S. Pat. No. 5,591,616, EP0604662, EP0672752, WO8603776, WO9209696, WO9419930, WO9967357, U.S. Pat. No. 4,399,216, WO8303259, U.S. Pat. No. 5,731,179, EP068730, WO9516031, U.S. Pat. Nos. 5,693,512, 6,051,757 and EP904362A1. *Agrobacterium*-mediated plant transformation involves as a first step the placement of DNA fragments cloned on plasmids into living *Agrobacterium* cells, which are then subsequently used for transformation into individual plant cells. *Agrobacterium*-mediated plant transformation is thus an indirect plant transformation method. Methods of *Agrobacterium*-mediated plant transformation that involve using vectors with no T-DNA are also well known to those skilled in the art and can have applicability in the present disclosure. See, for example, U.S. Pat. No. 7,250,554, which utilizes P-DNA instead of T-DNA in the transformation vector.

Direct plant transformation methods using DNA have also been reported. The first of these to be reported historically is electroporation, which utilizes an electrical current applied to a solution containing plant cells (M. E. Fromm et al., Nature, 319, 791 (1986); H. Jones et al., Plant Mol. Biol., 13, 501 (1989) and H. Yang et al., Plant Cell Reports, 7, 421 (1988). Another direct method, called "biolistic bombardment", uses ultrafine particles, usually tungsten or gold, that are coated with DNA and then sprayed onto the surface of a plant tissue with sufficient force to cause the particles to penetrate plant cells, including the thick cell wall, membrane and nuclear envelope, but without killing at least some of them (U.S. Pat. Nos. 5,204,253, 5,015,580). A third direct method uses fibrous forms of metal or ceramic consisting of sharp, porous or hollow needle-like projections that literally impale the cells, and also the nuclear envelope of cells. Both silicon carbide and aluminum borate whiskers have been used for plant transformation (Mizuno et al., 2004; Petolino et al., 2000; U.S. Pat. No. 5,302,523 US Application 20040197909) and also for bacterial and animal transformation (Kaepler et al., 1992; Raloff, 1990; Wang, 1995). There are other methods reported, and undoubtedly, additional methods will be developed. However, the efficiencies of each of these indirect or direct methods in introducing foreign DNA into plant cells are invariably extremely low, making it necessary to use some method for selection of only those cells that have been transformed, and further, allowing growth and regeneration into plants of only those cells that have been transformed.

For efficient plant transformation, a selection method must be employed such that whole plants are regenerated from a single transformed cell and every cell of the transformed plant carries the DNA of interest. These methods can employ positive selection, whereby a foreign gene is supplied to a plant cell that allows it to utilize a substrate present in the medium that it otherwise could not use, such as mannose or xylose (for example, refer U.S. Pat. No. 5,767,378; 5,994,629). More typically, however, negative selection is used because it is more efficient, utilizing selective agents such as herbicides or antibiotics that either kill or inhibit the growth of nontransformed plant cells and reducing the possibility of chimeras. Resistance genes that are effective against negative selective agents are provided on the introduced foreign DNA used for the plant transformation. For example, one of the most popular selective agents used is the antibiotic kanamycin, together with the resistance gene neomycin phosphotransferase (nptII), which confers resistance to kanamycin and related antibiotics (see, for example, Messing & Vierra, *Gene* 19: 259-268 (1982); Bevan et al., *Nature* 304:184-187 (1983)). However, many different antibiotics and antibiotic resistance genes can be used for transformation purposes (refer U.S. Pat. Nos. 5,034,322, 6,174,724 and 6,255,560). In addition, several herbicides and herbicide resistance genes have been used for transformation purposes, including the bar gene, which confers resistance to the herbicide phosphinothricin (White et al., *Nucl Acids Res* 18: 1062 (1990), Spencer et al., *Theor Appl Genet* 79: 625-631(1990), U.S. Pat. Nos. 4,795,855, 5,378, 824 and 6,107,549). In addition, the dhfr gene, which confers resistance to the anticancer agent methotrexate, has been used for selection (Bourouis et al., *EMBO J.* 2(7): 1099-1104 (1983).

Genes can be introduced in a site directed fashion using homologous recombination. Homologous recombination permits site specific modifications in endogenous genes and thus inherited or acquired mutations may be corrected, and/or novel alterations may be engineered into the genome.

Homologous recombination and site-directed integration in plants are discussed in, for example, U.S. Pat. Nos. 5,451, 513, 5,501,967 and 5,527,695.

Methods of producing transgenic plants are well known to those of ordinary skill in the art. Transgenic plants can now be produced by a variety of different transformation methods including, but not limited to, electroporation; microinjection; microprojectile bombardment, also known as particle acceleration or biolistic bombardment; viral-mediated transformation; and *Agrobacterium*-mediated transformation. See, for example, U.S. Pat. Nos. 5,405,765; 5,472,869; 5,538,877; 5,538,880; 5,550,318; 5,641,664; and 5,736,369; and International Patent Application Publication Nos. WO/2002/038779 and WO/2009/117555; Lu et al., (Plant Cell Reports, 2008, 27:273-278); Watson et al., Recombinant DNA, Scientific American Books (1992); Hinchee et al., Bio/Tech. 6:915-922 (1988); McCabe et al., Bio/Tech. 6:923-926 (1988); Toriyama et al., Bio/Tech. 6:1072-1074 (1988); Fromm et al., Bio/Tech. 8:833-839 (1990); Mullins et al., Bio/Tech. 8:833-839 (1990); Hiei et al., Plant Molecular Biology 35:205-218 (1997); Ishida et al., Nature Biotechnology 14:745-750 (1996); Zhang et al., Molecular Biotechnology 8:223-231 (1997); Ku et al., Nature Biotechnology 17:76-80 (1999); and, Raineri et al., Bio/Tech. 8:33-38 (1990)), each of which is expressly incorporated herein by reference in their entirety. Other references teaching the transformation of *cannabis* plants and the production of callus tissue include Raharjo et al 2006, "Callus Induction and Phytochemical Characterization of *Cannabis sativa* Cell Suspension Cultures", Indo. J. Chem 6 (1) 70-74; and "The biotechnology of *Cannabis sativa*" by Sam R. Zwenger, electronically published April, 2009.

Microprojectile bombardment is also known as particle acceleration, biolistic bombardment, and the gene gun (Biolistic® Gene Gun). The gene gun is used to shoot pellets that are coated with genes (e.g., for desired traits) into plant seeds or plant tissues in order to get the plant cells to then express the new genes. The gene gun uses an actual explosive (.22 caliber blank) to propel the material. Compressed air or steam may also be used as the propellant. The Biolistic® Gene Gun was invented in 1983-1984 at Cornell University by John Sanford, Edward Wolf, and Nelson Allen. It and its registered trademark are now owned by E. I. du Pont de Nemours and Company. Most species of plants have been transformed using this method.

*Agrobacterium tumefaciens* is a naturally occurring bacterium that is capable of inserting its DNA (genetic information) into plants, resulting in a type of injury to the plant known as crown gall. Most species of plants can now be transformed using this method, including cucurbitaceous species. A transgenic plant formed using *Agrobacterium* transformation methods typically contains a single gene on one chromosome, although multiple copies are possible. Such transgenic plants can be referred to as being hemizygous for the added gene. A more accurate name for such a plant is an independent segregant, because each transformed plant represents a unique T-DNA integration event (U.S. Pat. No. 6,156,953). A transgene locus is generally characterized by the presence and/or absence of the transgene. A heterozygous genotype in which one allele corresponds to the absence of the transgene is also designated hemizygous (U.S. Pat. No. 6,008,437).

General transformation methods, and specific methods for transforming certain plant species (e.g., maize) are described in U.S. Pat. Nos. 4,940,838, 5,464,763, 5,149,645, 5,501, 967, 6,265,638, 4,693,976, 5,635,381, 5,731,179, 5,693,512, 6,162,965, 5,693,512, 5,981,840, 6,420,630, 6,919,494, 6,329,571, 6,215,051, 6,369,298, 5,169,770, 5,376,543, 5,416,011, 5,569,834, 5,824,877, 5,959,179, 5,563,055, and 5,968,830, each of which is incorporated herein by reference in its entirety for all purposes.

Non-limiting examples of methods for transforming *cannabis* plants and *cannabis* tissue culture methods are described in Zweger (The Biotechnology of *Cannabis sativa*, April 2009); MacKinnon (Genetic transformation of *Cannabis sativa* Linn: a multipurpose fiber crop, doctoral thesis, University of Dundee, Scotland, 2003), MacKinnon et al. (Progress towards transformation of fiber hemp, Scottish Crop Research, 2000), and US 20120311744, each of which is herein incorporated by reference in its entirety for all purposes. The transformation can be physical, chemical and/or biological.

Herbicide Resistance

Numerous herbicide resistance genes are known and may be employed with the invention. A non-limiting example is a gene conferring resistance to a herbicide that inhibits the growing point or meristem such as imidazolinone or sulfonylurea herbicides. As imidazolinone and sulfonylurea herbicides are acetolactate synthase (ALS)-inhibiting herbicides that prevent the formation of branched chain amino acids, exemplary genes in this category code for ALS and AHAS enzymes as described, for example, by Lee et al., *EMBO* 1, 7:1241, 1988; Gleen et al., *Plant Molec. Biology,* 18:1185, 1992; and Miki et al., *Theor. Appl. Genet.,* 80:449, 1990. As a non-limiting example, a gene may be employed to confer resistance to the exemplary sulfonylurea herbicide nicosulfuron.

Resistance genes for glyphosate (resistance conferred by mutant 5-enolpyruvylshikimate-3-phosphate synthase (EPSPS) and aroA genes, respectively) and other phosphono compounds such as glufosinate (phosphinothricin acetyltransferase (PAT) and *Streptomyces hygroscopicus* phosphinothricin acetyltransferase (bar) genes) may also be used. See, for example, U.S. Pat. No. 4,940,835 to Shah et al., which discloses the nucleotide sequence of a form of EPSPS that can confer glyphosate resistance. Non-limiting examples of EPSPS transformation events conferring glyphosate resistance are provided by U.S. Pat. Nos. 6,040,497 and 7,632,985. The MON89788 event disclosed in U.S. Pat. No. 7,632,985 in particular is beneficial in conferring glyphosate tolerance in combination with an increase in average yield relative to prior events.

A DNA molecule encoding a mutant aroA gene can be obtained under ATCC Accession No. 39256, and the nucleotide sequence of the mutant gene is disclosed in U.S. Pat. No. 4,769,061 to Comai. A hygromycin B phosphotransferase gene from *E. coli* that confers resistance to glyphosate in tobacco callus and plants is described in Penaloza-Vazquez et al., *Plant Cell Reports,* 14:482, 1995. European Patent Application Publication No. EP0333033 to Kumada et al., and U.S. Pat. No. 4,975,374 to Goodman et al., disclose nucleotide sequences of glutamine synthetase genes that confer resistance to herbicides such as L-phosphinothricin. The nucleotide sequence of a phosphinothricin acetyltransferase gene is provided in European Patent Application Publication No. EP0242246 to Leemans et al. DeGreef et al. (*Biotechnology,* 7:61, 1989) describe the production of transgenic plants that express chimeric bar genes coding for phosphinothricin acetyl transferase activity. Exemplary genes conferring resistance to a phenoxy class herbicide haloxyfop and a cyclohexanedione class herbicide sethoxydim are the Acct-S1, Acct-S2 and Acct-S3 genes described by Marshall et al., (*Theor. Appl. Genet.,* 83:435, 1992). As a non-limiting example, a gene may confer resistance to other exemplary phenoxy class herbicides that include, but are not limited to, quizalofop-p-ethyl and 2,4-dichlorophenoxyacetic acid (2,4-D).

Genes are also known that confer resistance to herbicides that inhibit photosynthesis such as, for example, triazine herbicides (psbA and gs+ genes) and benzonitrile herbicides (nitrilase gene). As a non-limiting example, a gene may confer resistance to the exemplary benzonitrile herbicide bromoxynil. Przibila et al. (*Plant Cell,* 3:169, 1991) describe the transformation of *Chlamydomonas* with plasmids encoding mutant psbA genes. Nucleotide sequences for nitrilase genes are disclosed in U.S. Pat. No. 4,810,648 to Stalker, and DNA molecules containing these genes are available under ATCC Accession Nos. 53435, 67441, and 67442. Cloning and expression of DNA coding for a glutathione S-transferase is described by Hayes et al. (*Biochem. J.,* 285:173, 1992). 4-hydroxyphenylpyruvate dioxygenase (HPPD) is a target of the HPPD-inhibiting herbicides, which deplete plant plastoquinone and vitamin E pools. Rippert et al. (*Plant Physiol.,* 134:92, 2004) describes an HPPD-inhibitor resistant tobacco plant that was transformed with a yeast-derived prephenate dehydrogenase (PDH) gene. Protoporphyrinogen oxidase (PPO) is the target of the PPO-inhibitor class of herbicides; a PPO-inhibitor resistant PPO gene was recently identified in *Amaranthus tuberculatus* (Patzoldt et al., *PNAS,* 103(33):12329, 2006). The herbicide methyl viologen inhibits $CO_2$ assimilation. Foyer et al. (*Plant Physiol.,* 109:1047, 1995) describe a plant overexpressing glutathione reductase (GR) that is resistant to methyl viologen treatment.

Siminszky (*Phytochemistry Reviews,* 5:445, 2006) describes plant cytochrome P450-mediated detoxification of multiple, chemically unrelated classes of herbicides. Modified bacterial genes have been successfully demonstrated to confer resistance to atrazine, a herbicide that binds to the plastoquinone-binding membrane protein $Q_B$ in photosystem II to inhibit electron transport. See, for example, studies by Cheung et al. (*PNAS,* 85:391, 1988), describing tobacco plants expressing the chloroplast psbA gene from an atrazine-resistant biotype of *Amaranthus hybridus* fused to the regulatory sequences of a nuclear gene, and Wang et al. (*Plant Biotech. J.,* 3:475, 2005), describing transgenic alfalfa, *Arabidopsis*, and tobacco plants expressing the atzA gene from *Pseudomonas* sp. that were able to detoxify atrazine.

Bayley et al. (*Theor. Appl. Genet.,* 83:645, 1992) describe the creation of 2,4-D-resistant transgenic tobacco and cotton plants using the 2,4-D monooxygenase gene tfdA from *Alcaligenes eutrophus* plasmid pJP5. U.S. Patent Application Publication No. 20030135879 describes the isolation of a gene for dicamba monooxygenase (DMO) from *Psueodmonas maltophilia* that is involved in the conversion of dicamba to a non-toxic 3,6-dichlorosalicylic acid and thus may be used for producing plants tolerant to this herbicide.

Other examples of herbicide resistance have been described, for instance, in U.S. Pat. Nos. 6,803,501; 6,448, 476; 6,248,876; 6,225,114; 6,107,549; 5,866,775; 5,804, 425; 5,633,435; 5,463,175.

Disease and Pest Resistance

Plant defenses are often activated by specific interaction between the product of a disease resistance gene (R) in the plant and the product of a corresponding avirulence (Avr) gene in the pathogen. A plant line can be transformed with a cloned resistance gene to engineer plants that are resistant to specific pathogen strains. See, for example Jones et al. (*Science,* 266:789-793, 1994) (cloning of the tomato Cf-9 gene for resistance to *Cladosporium flavum*); Martin et al.

(*Science,* 262:1432-1436, 1993) (tomato Pto gene for resistance to *Pseudomonas syringae* pv. tomato); and Mindrinos et al. (*Cell,* 78(6):1089-1099, 1994) (*Arabidopsis* RPS2 gene for resistance to *Pseudomonas syringae*).

A viral-invasive protein or a complex toxin derived therefrom may also be used for viral disease resistance. For example, the accumulation of viral coat proteins in transformed plant cells imparts resistance to viral infection and/or disease development effected by the virus from which the coat protein gene is derived and related viruses. See Beachy et al. (*Ann. Rev. Phytopathol.,* 28:451, 1990). Coat protein-mediated resistance has been conferred upon transformed plants against alfalfa mosaic virus, cucumber mosaic virus, tobacco streak virus, potato virus X, potato virus Y, tobacco etch virus, tobacco rattle virus, and tobacco mosaic virus.

A virus-specific antibody may also be used. See, for example, Tavladoraki et al. (*Nature,* 366:469-472, 1993), who show that transgenic plants expressing recombinant antibody genes are protected from virus attack. Virus resistance has also been described in, for example, U.S. Pat. Nos. 6,617,496; 6,608,241; 6,015,940; 6,013,864; 5,850,023 and 5,304,730. Additional means of inducing whole-plant resistance to a pathogen include modulation of the systemic acquired resistance (SAR) or pathogenesis related (PR) genes, for example genes homologous to the *Arabidopsis thaliana* NIM1/NPR1/SAI1, and/or by increasing salicylic acid production (Ryals et al., *Plant Cell,* 8:1809-1819, 1996).

Logemann et al. (*Biotechnology,* 10:305-308, 1992), for example, disclose transgenic plants expressing a barley ribosome-inactivating gene that have an increased resistance to fungal disease. Plant defensins may be used to provide resistance to fungal pathogens (Thomma et al., *Planta,* 216:193-202, 2002). Other examples of fungal disease resistance are provided in U.S. Pat. Nos. 6,653,280; 6,573,361; 6,506,962; 6,316,407; 6,215,048; 5,516,671; 5,773,696; 6,121,436; and 6,316,407.

Nematode resistance has been described in, for example, U.S. Pat. No. 6,228,992, and bacterial disease resistance has been described in, for example, U.S. Pat. No. 5,516,671.

The use of the herbicide glyphosate for disease control in hemp plants containing event MON89788, which confers glyphosate tolerance, has also been described in U.S. Pat. No. 7,608,761.

Insect Resistance

One example of an insect resistance gene includes a *Bacillus thuringiensis* protein, a derivative thereof, or a synthetic polypeptide modeled thereon. See, for example, Geiser et al. (*Gene,* 48(1):109-118, 1986), who disclose the cloning and nucleotide sequence of a *Bacillus thuringiensis* δ-endotoxin gene. Moreover, DNA molecules encoding δ-endotoxin genes can be purchased from the American Type Culture Collection, Manassas, Va., for example, under ATCC Accession Nos. 40098, 67136, 31995 and 31998. Another example is a lectin. See, for example, Van Damme et al., (*Plant Molec. Biol.,* 24:825-830, 1994), who disclose the nucleotide sequences of several *Clivia miniata* mannose-binding lectin genes. A vitamin-binding protein may also be used, such as, for example, avidin. See PCT Application No. US93/06487, the contents of which are hereby incorporated by reference. This application teaches the use of avidin and avidin homologues as larvicides against insect pests.

Yet another insect resistance gene is an enzyme inhibitor, for example, protease, proteinase, or amylase inhibitors. See, for example, Abe et al. (*J. Biol. Chem.,* 262:16793-16797, 1987) describing the nucleotide sequence of a rice cysteine proteinase inhibitor; Linthorst et al. (*Plant Molec. Biol.,* 21:985-992, 1993) describing the nucleotide sequence of a cDNA encoding tobacco proteinase inhibitor I; and Sumitani et al. (*Biosci. Biotech. Biochem.,* 57:1243-1248, 1993) describing the nucleotide sequence of a *Streptomyces nitrosporeus* α-amylase inhibitor.

An insect-specific hormone or pheromone may also be used. See, for example, the disclosure by Hammock et al. (*Nature,* 344:458-461, 1990) of baculovirus expression of cloned juvenile hormone esterase, an inactivator of juvenile hormone; Gade and Goldsworthy (*Eds. Physiological System in Insects,* Elsevier Academic Press, Burlington, Mass., 2007), describing allostatins and their potential use in pest control; and Palli et al. (*Vitam. Horm.,* 73:59-100, 2005), disclosing use of ecdysteroid and ecdysteroid receptor in agriculture. The diuretic hormone receptor (DHR) was identified in Price et al. (*Insect Mol. Biol.,* 13:469-480, 2004) as another potential candidate target of insecticides.

Still other examples include an insect-specific antibody or an immunotoxin derived therefrom and a developmental-arrestive protein. See Taylor et al. (Seventh Int'l Symposium on Molecular Plant-Microbe Interactions, Edinburgh, Scotland, Abstract W97, 1994), who described enzymatic inactivation in transgenic tobacco via production of single-chain antibody fragments. Numerous other examples of insect resistance have been described. See, for example, U.S. Pat. Nos. 6,809,078; 6,713,063; 6,686,452; 6,657,046; 6,645,497; 6,642,030; 6,639,054; 6,620,988; 6,593,293; 6,555,655; 6,538,109; 6,537,756; 6,521,442; 6,501,009; 6,468,523; 6,326,351; 6,313,378; 6,284,949; 6,281,016; 6,248,536; 6,242,241; 6,221,649; 6,177,615; 6,156,573; 6,153,814; 6,110,464; 6,093,695; 6,063,756; 6,063,597; 6,023,013; 5,959,091; 5,942,664; 5,942,658, 5,880,275; 5,763,245 and 5,763,241.

Resistance to Abiotic Stress

Abiotic stress includes dehydration or other osmotic stress, salinity, high or low light intensity, high or low temperatures, submergence, exposure to heavy metals, and oxidative stress. Delta-pyrroline-5-carboxylate synthetase (PSCS) from mothbean has been used to provide protection against general osmotic stress. Mannitol-1-phosphate dehydrogenase (mt1D) from *E. coli* has been used to provide protection against drought and salinity. Choline oxidase (codA from *Arthrobactor globiformis*) can protect against cold and salt. *E. coli* choline dehydrogenase (betA) provides protection against salt. Additional protection from cold can be provided by omega-3-fatty acid desaturase (fad7) from *Arabidopsis thaliana*. Trehalose-6-phosphate synthase and levan sucrase (SacB) from yeast and *Bacillus subtilis,* respectively, can provide protection against drought (summarized from Annex II Genetic Engineering for Abiotic Stress Tolerance in Plants, Consultative Group On International Agricultural Research Technical Advisory Committee). Overexpression of superoxide dismutase can be used to protect against superoxides, see U.S. Pat. No. 5,538,878.

Additional Traits

Additional traits can be introduced into the hemp variety of the present invention. A non-limiting example of such a trait is a coding sequence which decreases RNA and/or protein levels. The decreased RNA and/or protein levels may be achieved through RNAi methods, such as those described in U.S. Pat. No. 6,506,559.

Another trait that may find use with the hemp variety of the invention is a sequence which allows for site-specific recombination. Examples of such sequences include the FRT sequence used with the FLP recombinase (Zhu and Sadowski, *J. Biol. Chem.,* 270:23044-23054, 1995) and the LOX sequence used with CRE recombinase (Sauer, *Mol.*

Cell. Biol., 7:2087-2096, 1987). The recombinase genes can be encoded at any location within the genome of the hemp plant and are active in the hemizygous state.

In certain embodiments hemp plants may be made more tolerant to or more easily transformed with *Agrobacterium tumefaciens*. For example, expression of p53 and iap, two baculovirus cell-death suppressor genes, inhibited tissue necrosis and DNA cleavage. Additional targets may include plant-encoded proteins that interact with the *Agrobacterium* Vir genes; enzymes involved in plant cell wall formation; and histones, hi stone acetyltransferases and hi stone deacetylases (reviewed in Gelvin, *Microbiology & Mol. Biol. Reviews*, 67:16-37, 2003).

In addition to the modification of oil, fatty acid, or phytate content described above, certain embodiments may modify the amounts or levels of other compounds. For example, the amount or composition of antioxidants can be altered. See, for example, U.S. Pat. Nos. 6,787,618 and 7,154,029 and International Patent Application Publication No. WO 00/68393, which disclose the manipulation of antioxidant levels, and International Patent Application Publication No. WO 03/082899, which discloses the manipulation of an antioxidant biosynthetic pathway.

Additionally, seed amino acid content may be manipulated. U.S. Pat. No. 5,850,016 and International Patent Application Publication No. WO 99/40209 disclose the alteration of the amino acid compositions of seeds. U.S. Pat. Nos. 6,080,913 and 6,127,600 disclose methods of increasing accumulation of essential amino acids in seeds.

U.S. Pat. No. 5,559,223 describes synthetic storage proteins of which the levels of essential amino acids can be manipulated. International Patent Application Publication No. WO 99/29882 discloses methods for altering amino acid content of proteins. International Patent Application Publication No. WO 98/20133 describes proteins with enhanced levels of essential amino acids. International Patent Application Publication No. WO 98/56935 and U.S. Pat. Nos. 6,346,403; 6,441,274; and 6,664,445 disclose plant amino acid biosynthetic enzymes. International Patent Application Publication No. WO 98/45458 describes synthetic seed proteins having a higher percentage of essential amino acids than wild-type.

U.S. Pat. No. 5,633,436 discloses plants comprising a higher content of sulfur-containing amino acids; U.S. Pat. No. 5,885,801 discloses plants comprising a high threonine content; U.S. Pat. Nos. 5,885,802 and 5,912,414 disclose plants comprising a high methionine content; U.S. Pat. No. 5,990,389 discloses plants comprising a high lysine content; U.S. Pat. No. 6,459,019 discloses plants comprising an increased lysine and threonine content; International Patent Application Publication No. WO 98/42831 discloses plants comprising a high lysine content; International Patent Application Publication No. WO 96/01905 discloses plants comprising a high threonine content; and International Patent Application Publication No. WO 95/15392 discloses plants comprising a high lysine content.

Cannabis Hemp Extracts and Compositions

In some embodiments, the present disclosure provides for extracts and compositions from the hemp plants of the present disclosure. *Cannabis* extracts or products or the present disclosure include:

Solvent reduced oils-also sometimes known as oil, BHO, $CO_2$ extract, among other names. This type of extract is made by soaking plant material in a chemical solvent capable of solubilizing one or more chemical constituents of the plant (e.g., cannabinoids and/or terpenes). After separating the solvent from plant material, the solvent can be boiled or evaporated off, leaving the extract "oil" behind. Butane Hash Oil is produced by passing butane over *cannabis* and then letting the butane evaporate. Rick Simpson Oil is produced through isopropyl, or ethanol extraction of *cannabis*. The resulting substance is a wax like golden brown paste. Another common extraction solvent for creating *cannabis* oil is $CO_2$. Persons having skill in the art will be familiar with $CO_2$ extraction techniques and devices, including those disclosed in US 20160279183, US 2015/01505455, U.S. Pat. No. 9,730,911, and US 2018/0000857.

Heat extractions—The present disclosure also teaches extracts produced via heat-based extraction methods, such as those disclosed in US Patent Application Nos. US 2018/0078874, US 2019/0151771, US 2019/0076753, and U.S. Pat. No. 10,159,908, each of which is hereby incorporated by reference for all purposes. In some embodiments, the plants of the present disclosure can be extracted by exposing tissue to a hot air gas stream that volatizes cannabinoids and/or other secondary metabolites of the plant, which are then condensed and recovered in tanks.

In some embodiments, the present disclosure teaches exposing plants, plant parts or plant cells to vaporizing heat. As used herein, the term "vaporizing heat" refers to heat sufficient to volatize one or more terpene on cannabinoid components of said plant, plant part or plant cell. The boiling points for each of the cannabinoid and terpene constituents of a hemp plant are well known or readily ascertainable. In some embodiments, vaporizing heat comprises 150° F., 155° F., 160° F., 165° F., 170° F., 175° F., 180° F., 185° F., 190° F., 195° F., 200° F., 205° F., 210° F., 215° F., 220° F., 225° F., 230° F., 235° F., 240° F., 245° F., 250° F., 255° F., 260° F., 265° F., 270° F., 275° F., 280° F., 285° F., 290° F., 295° F., 300° F. ° F., 305° F. ° F., 310° F. ° F., 315° F. ° F., 320° F. ° F., 325° F. ° F., 330° F. ° F., 335° F. ° F., 340° F. ° F., 345° F., or 350° F., and all ranges and subranges therebetween.

Tinctures—are alcoholic extracts of *cannabis*. These are usually made by mixing *cannabis* material with high proof ethanol and separating out plant material. Within the dietary supplement industry "tincture" may also describe an oil dilution of hemp extract.

In some embodiments, the specialty *cannabis* of the present disclosure is extracted via methods that preserve the cannabinoid and terpenes. In other embodiments, said methods can be used with any *cannabis* plants. The extracts of the present disclosure are designed to produce products for human or animal consumption via inhalation (via combustion, vaporization and nebulization), buccal absorption within the mouth, oral administration (e.g., eating/drinking), and topical application delivery methods.

The chemical extraction of specialty *cannabis* can be accomplished employing polar and non-polar solvents in various phases at varying pressures and temperatures to selectively or comprehensively extract terpenes, cannabinoids and other compounds of flavor, fragrance or pharmacological value for use individually or combination in the formulation of our products. The solvents employed for selective extraction of our cultivars may include water, carbon dioxide, 1,1,1,2-tetrafluoroethane, butane, propane, ethanol, isopropyl alcohol, hexane, and limonene, in combination or series. It is also possible to extract compounds of interest mechanically by sieving the plant parts that produce those compounds. Measuring the plant part, i.e. trichome gland head, to be sieved via optical or electron microscopy can aid the selection of the optimal sieve pore size, ranging from 30 to 130 microns, to capture the plant part of interest. The chemical and mechanical extraction methods of the present disclosure can be used to produce products that combine chemical extractions with plant parts containing compounds of interest.

The extracts of the present disclosure may also be combined with pure compounds of interest to the extractions, e.g. cannabinoids or terpenes to further enhance or modify the resulting formulation's fragrance, flavor or pharmacology. Thus, in some embodiments, the present disclosure teaches compositions comprising at least one ingredient extracted from the 'CW1AS1' plant. In some embodiments, extracts from the hemp lines of the present disclosure are combined with one or more additional compounds. In some embodiments, extracts of the present disclosure, such as whole hemp extracts, or a purified cannabinoid from said hemp plant, can be combined with another cannabinoid or terpene to produce a composition.

The compositions of the present disclosure encompass many forms. In some embodiments, the present disclosure provides CBD oils and tinctures. In some embodiments, the present disclosure provides CBD capsules. In some embodiments, the present disclosure provides CBD infused edibles, such as gummies, gum, lollipops, taffy, cookies, brownies, ice cream, chocolate, jerky, animal dry and wet foods, animal treats, etc. In some embodiments, the present disclosure provides for cosmetics comprising CBD, such as lip stick, balms, creams, shampoo, conditioners, lotions, rubbing oils, lubricants, Etc. In some embodiments, the CBD oils comprise extracts from 'CW1AS1', such as solvent extracted oils, heat extracted oils. In some embodiments, the capsules comprise extracts from 'CW1AS1.'

In some embodiments, the present disclosure teaches hemp commodity products, including processed hemp inflorescences, fiber, hemp extract, cannabinoids, and terpenes. As used herein, the term "processed hemp inflorescences" means inflorescences from a hemp plant that have been harvested and dried to a moisture content of less than 20% wt./wt. In some embodiments, the processed hemp inflorescences are ground or broken up in smaller pieces.

Deposit Information

A deposit of the 'CW1AS1' hemp cultivar is maintained by CWB Holdings, Inc., 1720 S Bellaire St. Suite 600, Denver, Colo. 80222, USA. In addition, a sample of 2500 seeds of the 'CW1AS1' variety of this disclosure has been deposited with an International Depositary Authority as established under the Budapest Treaty according to 37 CFR 1.803(a)(1), at the National Collections of Industrial, Food and Marine Bacteria (NCIMB), Ferguson Building, Craibstone Estate, Bucksburn, Aberdeen, AB21 9YA, Scotland.

The 'CW1AS1' seeds were deposited as NCIMB 43291 on Nov. 23, 2018.

To satisfy the enablement requirements of 35 U.S.C. 112, and to certify that the deposit of the isolated strain (i.e., hemp plant) of the present disclosure meets the criteria set forth in 37 C.F.R. 1.801-1.809 and Manual of Patent Examining Procedure (MPEP) 2402-2411.05, Applicants hereby make the following statements regarding the deposited 'CW1AS1' hemp cultivar (deposited as NCIMB 43291):

1. During the pendency of this application, access to the disclosure will be afforded to the Commissioner upon request;
2. All restrictions on availability to the public will be irrevocably removed upon granting of the patent under conditions specified in 37 CFR 1.808;
3. The deposit will be maintained in a public repository for a period of 30 years or 5 years after the last request or for the effective life of the patent, whichever is longer;
4. A test of the viability of the biological material at the time of deposit will be conducted by the public depository under 37 C.F.R. 1.807; and
5. The deposit will be replaced if it should ever become unavailable.

Access to this deposit will be available during the pendency of this application to persons determined by the Commissioner of Patents and Trademarks to be entitled thereto under 37 C.F.R. § 1.14 and 35 U.S.C. § 122. Upon allowance of any claims in this application, all restrictions on the availability to the public of the variety will be irrevocably removed by affording access to a deposit of at least 2,500 seeds of the same variety with the NCIMB.

Unless defined otherwise, all technical and scientific terms herein have the same meaning as commonly understood by one of ordinary skill in the art to which this invention belongs. Although any methods and materials, similar or equivalent to those described herein, can be used in the practice or testing of the present invention, the non-limiting exemplary methods and materials are described herein.

All publications and patent applications mentioned in the specification are indicative of the level of those skilled in the art to which this invention pertains. All publications and patent applications are herein incorporated by reference to the same extent as if each individual publication or patent application was specifically and individually indicated to be incorporated by reference. Nothing herein is to be construed as an admission that the present disclosure is not entitled to antedate such publication by virtue of prior disclosure.

Many modifications and other embodiments of the disclosures set forth herein will come to mind to one skilled in the art to which these disclosures pertain having the benefit of the teachings presented in the foregoing descriptions and the associated drawings. Therefore, it is to be understood that the disclosures are not to be limited to the specific embodiments disclosed and that modifications and other embodiments are intended to be included within the scope of the appended claims. Although specific terms are employed herein, they are used in a generic and descriptive sense only and not for purposes of limitation.

While the disclosure has been described in connection with specific embodiments thereof, it will be understood that it is capable of further modifications and this application is intended to cover any variations, uses, or adaptations of the disclosure following, in general, the principles of the disclosure and including such departures from the present disclosure as come within known or customary practice within the art to which the disclosure pertains and as may be applied to the essential features hereinbefore set forth and as follows in the scope of the appended claims.

Example 1. Cannabinoid Potency Tests

Samples of inflorescences from the 'CW1AS1' hemp line harvested at maturity were provided to a third party vendor for analysis. Three samples of the 'CW1AS1' inflorescences were analyzed by Botanacor Services using high performance liquid chromatography. The results of these analyses are provided below in Table 6.

TABLE 6

Cannabinoid Potency Analysis Results for 'CW1AS1'

| Analysis | THC Potential | CBD Potential |
| --- | --- | --- |
| 1 | 0.26% | 6.68% |
| 2 | 0.26% | 6.87% |
| 3 | 0.27% | 6.99% |
| 4 | 0.21% | 7.28% |
| 5 | 0.24% | 7.29% |
| 6 | 0.20% | 7.32% |

INCORPORATION BY REFERENCE

All references, articles, publications, patents, patent publications, and patent applications cited herein are incorporated by reference in their entireties for all purposes. However, mention of any reference, article, publication, patent, patent publication, and patent application cited herein is not, and should not be taken as, an acknowledgment or any form of suggestion that they constitute valid prior art or form part of the common general knowledge in any country in the world.

NUMBERED EMBODIMENTS

Further embodiments contemplated by the disclosure are listed below.

1. A seed, plant, plant part, or plant cell of hemp plant variety designated 'CW1AS1', wherein representative seed of the variety has been deposited under NCIMB No. 43291.

2. The hemp plant part of embodiment 1, wherein the plant part is an inflorescence.

3. A hemp plant or a plant part or a plant cell thereof, having all of the characteristics of the hemp plant variety designated 'CW1AS1' listed in Tables 1-5.

4. A hemp plant, or a plant part or a plant cell thereof, having all of the physiological and morphological characteristics of the hemp plant of any one of embodiments 1-3.

5. A hemp plant, or a part or a plant cell thereof, having all of the physiological and morphological characteristics of the hemp plant variety designated 'CW1AS1', wherein a representative sample of seed of said variety was deposited under NCIMB No. 43291.

6. A tissue culture of regenerable cells produced from the plant, plant part or plant cell of any one of embodiments 1-5, wherein a new plant regenerated from the tissue culture has all of the characteristics of the hemp plant variety designated 'CW1AS1' listed in Tables 1-5 when grown under the same environmental conditions.

7. A hemp plant regenerated from the tissue culture of embodiment 6, said plant having all the characteristics of the hemp plant variety designated 'CW1AS1' listed in Tables 1-5 when grown under the same environmental conditions.

8. A hemp plant regenerated from the tissue culture of embodiment 6, wherein the regenerated plant has all of the characteristics of the hemp plant variety designated CW1AS1', wherein a representative sample of seed of said variety was deposited under NCIMB No. 43291.

9. A method for producing a hemp seed, comprising a) selfing the hemp plant of any one of embodiments 1-5 and 7-8, and b) harvesting the resultant hemp seed.

10. A hemp seed produced by the method of embodiment 9.

11. A method for producing a hemp seed comprising crossing the hemp plant of any one of embodiments 1-5 and 7-8 with a second, distinct plant.

12. An F1 hemp seed produced by the method of embodiment 11.

13. An F1 hemp plant, or a part or a plant cell thereof, produced by growing the seed of embodiment 12.

14. A method of producing a hemp plant derived from the variety 'CW1AS1,' comprising: a) crossing the plant of any one of embodiments 1-5 and 7-8, with itself or a second plant to produce progeny seed; b) growing the progeny seed to produce a progeny plant and crossing the progeny plant with itself or a second plant to produce further progeny seed; and c) repeating steps (a) and (b) with sufficient inbreeding until a seed of an hemp plant derived from the variety 'CW1AS1' is produced.

15. The method of embodiment 14, further comprising crossing the hemp plant derived from the variety 'CW1AS1,' with a plant of a different genotype to produce seed of a hybrid plant derived from the hemp variety 'CW1AS1.'

16. A method for producing nucleic acids, the method comprising isolating nucleic acids from the seed, plant, plant part, or plant cell of any one of embodiments 1-15.

17. The hemp plant of any one of embodiments 1-5 and 7-8, comprising a single locus conversion and otherwise essentially all of the characteristics of the hemp plant of any one of embodiments 1-5 and 7-8 when grown in the same environmental conditions.

18. The hemp plant of embodiment 17, wherein the single locus conversion confers said plant with herbicide resistance.

19. The hemp plant of embodiment 17, wherein the single locus conversion is an artificially mutated gene or nucleotide sequence.

20. The hemp plant of embodiment 17, wherein the single locus conversion is a gene that has been modified through the use of breeding techniques.

21. A cultivar of hemp designated 'CW1AS1' as described and detailed herein.

22. A method of producing a cannabinoid extract, said method comprising the steps a) contacting the plant of any one of embodiments 1-5 and 7-8 with a solvent, thereby producing a cannabinoid extract.

23. A dry, sinsemilla non-viable plant or part thereof, wherein seed of hemp plants producing said dry plant and part thereof has been deposited under NCIMB No. 43291.

24. An assemblage of dry, non-viable sinsemilla female inflorescences from a hemp plant variety designated 'CW1AS1' wherein representative seed of the variety has been deposited under NCIMB No. 43291.

25. The dry, non-viable plant part of embodiment 23 or 24, wherein the plant part is an inflorescence.

26. The dry, non-viable plant part of embodiment 23 or 24, wherein the plant part is a trichome.

27. Dry, non-viable kief powder comprising cannabidiol (CBD), wherein seed of hemp plants producing said kief has been deposited under NCIMB No. 43291.

28. A method of producing a hemp plant with cannabidiol (CBD), said method comprising propagating a vegetative cutting from a hemp plant variety designated 'CW1AS1' wherein representative seed of the variety has been deposited under NCIMB No. 43291.

29. The hemp plant with CBD, produced according to the methods of embodiment 28.

30. The hemp plant of embodiment 5, wherein the plant is asexually reproduced.

31. A method for producing a hemp plant with inflorescences that produce cannabidiol (CBD), said method comprising: propagating a vegetative cutting from a stock hemp plant, thereby producing the hemp plant having CBD; wherein the stock hemp plant is a product of applying a plant breeding technique to a variety designated 'CW1AS1', wherein representative seed of the variety has been deposited under NCIMB No. 43291.

32. The method of embodiment 31, wherein said plant breeding technique is recurrent selection.

33. The method of embodiment 31, wherein said plant breeding technique is mass selection.

34. The method of embodiment 31, wherein said plant breeding technique is hybridization.

35. The method of embodiment 31, wherein said plant breeding technique is open-pollination.

36. The method of embodiment 31, wherein said plant breeding technique is backcrossing.

37. The method of embodiment 31, wherein said plant breeding technique is pedigree breeding.

38. The method of embodiment 31, wherein said plant breeding technique is mutation breeding, and wherein said mutation selected is spontaneous or artificially induced.

39. The hemp plant of embodiment 5, wherein the plant is capable of producing an asexual clone of said hemp plant.

40. The hemp plant of embodiment 39, wherein the asexual clone is capable of producing said hemp plant of embodiment 1.

41. A method for producing a new hemp plant, said method comprising: propagating a vegetative cutting from a stock hemp plant, thereby producing the new hemp plant; wherein the stock hemp plant is a product of a single cross between: a parental line plant with another plant, or with itself; wherein the parental line has been deposited under NCIMB No. 43291.

42. A method for producing a new hemp plant, said method comprising: propagating a vegetative cutting from a stock hemp plant, thereby producing the new hemp plant; wherein the stock hemp plant is a product of applying a plant breeding technique to a parental line plant; wherein the parental line has been deposited under NCIMB No. 43291.

43. The method of embodiment 42, wherein said plant breeding technique is recurrent selection.

44. The method of embodiment 42, wherein said plant breeding technique is mass selection.

45. The method of embodiment 42, wherein said plant breeding technique is hybridization.

46. The method of embodiment 42, wherein said plant breeding technique is open-pollination.

47. The method of embodiment 42, wherein said plant breeding technique is backcrossing.

48. The method of embodiment 42, wherein said plant breeding technique is pedigree breeding.

49. The method of embodiment 42, wherein said plant breeding technique is mutation breeding, and wherein said mutation selected is spontaneous or artificially induced.

50. The method of embodiment 42, wherein said plant breeding technique is marker enhanced selection.

What is claimed is:

1. A method for producing a *Cannabis* plant derived from a hemp variety designated 'CW1AS1', said method comprising crossing 'CW1AS1' with another *Cannabis* plant, thereby producing a progeny *Cannabis* plant; wherein representative seed of the 'CW1AS1' variety has been deposited under NCIMB No. 43291.

2. The method of claim 1, further comprising the steps of:
   a) crossing the progeny *Cannabis* plant from a previous step with itself or another *Cannabis* plant to produce a progeny *Cannabis* plant of a subsequent generation;
   b) repeating step (a) for one or more additional generations to produce a *Cannabis* plant further derived from the hemp variety designated 'CW1AS1'.

3. The method of claim 2, further comprising the step of contacting the *Cannabis* plant further derived from the hemp variety designated 'CW1AS1' or a plant part derived therefrom with a solvent, or exposing said *Cannabis* plant or plant part to vaporizing heat, thereby producing a cannabinoid extract.

4. A method for producing a *Cannabis* plant derived from a hemp variety designated 'CW1AS1', said method comprising:
   propagating a vegetative cutting from a stock *Cannabis* plant, thereby producing the *Cannabis* plant derived from the hemp variety designated 'CW1AS1';
   wherein the stock *Cannabis* plant is a product of applying a plant breeding technique to 'CW1AS1',
   wherein representative seed of the 'CW1AS1' variety has been deposited under NCIMB No. 43291.

5. The method of claim 4, further comprising the step of contacting the *Cannabis* plant derived from the hemp variety designated 'CW1AS1' or a plant part derived therefrom with a solvent, or exposing said *Cannabis* plant or plant part to vaporizing heat, thereby producing a cannabinoid extract.

6. The method of claim 4, wherein said plant breeding technique is recurrent selection.

7. The method of claim 4, wherein said plant breeding technique is mass selection.

8. The method of claim 4, wherein said plant breeding technique is hybridization.

9. The method of claim 4, wherein said plant breeding technique is open-pollination.

10. The method of claim 4, wherein said plant breeding technique is backcrossing.

11. The method of claim 4, wherein said plant breeding technique is pedigree breeding.

12. The method of claim 4, wherein said plant breeding technique is mutation breeding, and wherein said mutation selected is spontaneous or artificially induced.

13. The method of claim 4, wherein said plant breeding technique is marker enhanced selection.

14. A method for producing a *Cannabis* plant derived from a hemp variety designated 'CW1AS1', said method comprising:
   crossing a stock *Cannabis* plant with itself or another *Cannabis* plant, thereby producing the *Cannabis* plant derived from the hemp variety designated 'CW1AS1';
   wherein the stock *Cannabis* plant is a product of applying a plant breeding technique to 'CW1AS1',
   wherein representative seed of the 'CW1AS1' variety has been deposited under NCIMB No. 43291.

15. The method of claim 14, further comprising the step of contacting the *Cannabis* plant derived from the hemp variety designated 'CW1AS1' or a plant part derived therefrom with a solvent, or exposing said *Cannabis* plant or plant part to vaporizing heat, thereby producing a cannabinoid extract.

16. The method of claim 14, wherein said plant breeding technique is recurrent selection.

17. The method of claim 14, wherein said plant breeding technique is mass selection.

18. The method of claim 14, wherein said plant breeding technique is hybridization.

19. The method of claim 14, wherein said plant breeding technique is open-pollination.

20. The method of claim 14, wherein said plant breeding technique is backcrossing.

21. The method of claim 14, wherein said plant breeding technique is pedigree breeding.

22. The method of claim 14, wherein said plant breeding technique is mutation breeding, and wherein said mutation selected is spontaneous or artificially induced.

23. The method of claim 14, wherein said plant breeding technique is marker enhanced selection.

* * * * *